United States Patent
Demopulos et al.

(10) Patent No.: US 9,278,101 B2
(45) Date of Patent: *Mar. 8, 2016

(54) OPHTHALMOLOGIC IRRIGATION SOLUTIONS AND METHOD

(71) Applicant: Omeros Corporation, Seattle, WA (US)

(72) Inventors: Gregory A. Demopulos, Mercer Island, WA (US); Pamela Pierce Palmer, San Francisco, CA (US); Jeffrey M. Herz, Mill Creek, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/186,146

(22) Filed: Feb. 21, 2014

(65) Prior Publication Data

US 2014/0235597 A1   Aug. 21, 2014

Related U.S. Application Data

(63) Continuation of application No. 13/420,440, filed on Mar. 14, 2012, now abandoned, which is a continuation of application No. 12/799,981, filed on May 5, 2010, now Pat. No. 8,173,707, which is a continuation of application No. 10/630,626, filed on Jul. 30, 2003, now abandoned.

(60) Provisional application No. 60/399,899, filed on Jul. 30, 2002.

(51) Int. Cl.

| | | |
|---|---|---|
| *A61K 31/519* | (2006.01) | |
| *A61K 31/13* | (2006.01) | |
| *A61K 31/045* | (2006.01) | |
| *A61K 31/5377* | (2006.01) | |
| *A61K 9/00* | (2006.01) | |
| *A61K 31/00* | (2006.01) | |
| *A61K 45/06* | (2006.01) | |
| *A61K 31/137* | (2006.01) | |
| *A61K 31/167* | (2006.01) | |
| *A61K 31/192* | (2006.01) | |
| *A61K 31/4164* | (2006.01) | |
| *A61K 31/445* | (2006.01) | |
| *A61K 31/4174* | (2006.01) | |
| *A61K 31/4409* | (2006.01) | |
| *A61K 31/573* | (2006.01) | |

(52) U.S. Cl.
CPC ........... *A61K 31/5377* (2013.01); *A61K 9/0048* (2013.01); *A61K 31/00* (2013.01); *A61K 31/137* (2013.01); *A61K 31/167* (2013.01); *A61K 31/192* (2013.01); *A61K 31/4164* (2013.01); *A61K 31/4174* (2013.01); *A61K 31/445* (2013.01); *A61K 31/4409* (2013.01); *A61K 31/573* (2013.01); *A61K 45/06* (2013.01)

(58) Field of Classification Search
CPC ... A61K 31/00; A61K 31/137; A61K 31/167; A61K 31/192; A61K 31/4164; A61K 31/4174; A61K 31/4409; A61K 31/445; A61K 31/5377; A61K 31/573; A61K 45/06; A61K 9/0048
See application file for complete search history.

(56) References Cited

U.S. PATENT DOCUMENTS

| | | |
|---|---|---|
| 4,474,751 A | 10/1984 | Haslam et al. |
| 4,474,811 A | 10/1984 | Masuda et al. |
| 4,550,022 A | 10/1985 | Garabedian et al. |
| 4,876,250 A | 10/1989 | Clark |
| 4,938,970 A | 7/1990 | Hustead et al. |
| 5,110,493 A | 5/1992 | Cherng-Chyi et al. |
| 5,212,196 A | 5/1993 | House et al. |
| 5,298,487 A | 3/1994 | Chen et al. |
| 5,371,078 A | 12/1994 | Clark et al. |
| 5,523,316 A | 6/1996 | Gan et al. |
| 5,587,175 A | 12/1996 | Viegas et al. |
| 5,612,027 A | 3/1997 | Galin et al. |
| 5,624,893 A | 4/1997 | Yanni |
| 5,696,091 A | 12/1997 | York et al. |
| 5,759,532 A | 6/1998 | Galin et al. |
| 5,767,105 A | 6/1998 | Peyman |
| 5,798,356 A | 8/1998 | Doshi |
| 5,800,385 A | 9/1998 | Demopulos et al. |
| 5,811,446 A | 9/1998 | Thomas |

(Continued)

FOREIGN PATENT DOCUMENTS

| | | |
|---|---|---|
| EP | 0364266 A2 | 4/1990 |
| EP | 0 550 921 A1 | 7/1993 |

(Continued)

OTHER PUBLICATIONS

U.S. Appl. No. 14/075,588, filed Nov. 8, 2013, Demopulos et al.
Corbett et al., "Intraocular adrenaline maintains mydriasis during cataract surgery," *Br. J Ophthalmol*. 78:95-98 (1994).
Gillart et al., "Effects of Local Clonidine for Prolongation of Akinesia After Peribulbar Block," *Anesthesiology* 31(3A):A941-A942 (1994).
Grond, S., et al., "Inhibition of Synovial Plasma Extravasation by Preemptive Administration of an Antiinflammatory Irrigation Solution in the Rat Knee," *Anesth Analg* 92:1301-6 (2001).
Malhotra et al., "Comparison of the cardiovasculare effects of 2.5% phenylephrine and 10% phenylephrine during ophthalmic surgery," *Eye* 12:973-975 (1998).

(Continued)

*Primary Examiner* — Abigail Fisher
(74) *Attorney, Agent, or Firm* — Marcia S. Kelbon

(57) ABSTRACT

Solutions for perioperative intraocular application by continuous irrigation during ophthalmologic procedures are provided. These solutions include multiple agents that act to inhibit inflammation, inhibit pain, effect mydriasis (dilation of the pupil), and/or decrease intraocular pressure, wherein the multiple agents are selected to target multiple molecular targets to achieve multiple differing physiologic functions, and are included in dilute concentrations in a balanced salt solution carrier.

13 Claims, No Drawings

(56) References Cited

U.S. PATENT DOCUMENTS

| | | | |
|---|---|---|---|
| 5,820,583 A | 10/1998 | Demopulos et al. | |
| 5,858,017 A | 1/1999 | Demopulos et al. | |
| 5,860,950 A | 1/1999 | Demopulos et al. | |
| 5,972,326 A | 10/1999 | Galin et al. | |
| 6,030,974 A | 2/2000 | Schwartz et al. | |
| 6,056,715 A | 5/2000 | Demopulos et al. | |
| 6,117,907 A | 9/2000 | Sher | |
| 6,210,394 B1 | 4/2001 | Demopulos et al. | |
| 6,218,428 B1 | 4/2001 | Chynn | |
| 6,242,447 B1 | 6/2001 | Demopulos et al. | |
| 6,254,585 B1 | 7/2001 | Demopulos et al. | |
| 6,261,279 B1 | 7/2001 | Demopulos et al. | |
| 6,280,745 B1 | 8/2001 | Flore et al. | |
| 6,350,781 B1 | 2/2002 | Shahinia | |
| 6,395,746 B1 | 5/2002 | Cagle et al. | |
| 6,413,961 B1 | 7/2002 | Demopulos et al. | |
| 6,420,432 B2 | 7/2002 | Demopulos et al. | |
| 6,492,332 B1 | 12/2002 | Demopulos et al. | |
| 6,495,598 B1 | 12/2002 | Yoneda et al. | |
| 6,562,873 B2 | 5/2003 | Olejnik et al. | |
| 6,645,168 B2 | 11/2003 | Demopulos et al. | |
| 7,091,181 B2 | 8/2006 | Demopulos et al. | |
| 7,973,068 B2 | 7/2011 | Demopulos et al. | |
| 8,173,707 B2 | 5/2012 | Demopulos et al. | |
| 8,586,633 B2 | 11/2013 | Demopulos et al. | |
| 2002/0071874 A1 | 6/2002 | Olejnik et al. | |
| 2002/0128267 A1 | 9/2002 | Bandyopadhyay et al. | |
| 2002/0183279 A1 | 12/2002 | Tanaka | |
| 2003/0017199 A1 | 1/2003 | Woodward et al. | |
| 2003/0087962 A1 | 5/2003 | Demopulos et al. | |
| 2003/0191187 A1 | 10/2003 | Lee et al. | |
| 2004/0072809 A1 | 4/2004 | Demopulos et al. | |
| 2010/0311688 A1 | 12/2010 | Chapin et al. | |
| 2010/0311705 A1 | 12/2010 | Demopulos et al. | |
| 2011/0105450 A1 | 5/2011 | Chapin et al. | |
| 2012/0022094 A1 | 1/2012 | Harris et al. | |
| 2013/0079344 A1 | 3/2013 | Demopulos et al. | |
| 2014/0221326 A1 | 8/2014 | Demopulos et al. | |

FOREIGN PATENT DOCUMENTS

| | | |
|---|---|---|
| EP | 0 903 151 A1 | 3/1999 |
| JP | 9-506620 | 6/1995 |
| JP | 2001-516258 | 9/2001 |
| JP | 2002 161032 A2 | 6/2002 |
| JP | 2002161032 A2 | 6/2002 |
| WO | WO 87/07141 | 12/1987 |
| WO | WO 91/02527 | 3/1991 |
| WO | WO 92/04008 | 3/1992 |
| WO | WO 94/08602 | 4/1994 |
| WO | WO 95/09003 | 4/1995 |
| WO | WO 95/16435 | 6/1995 |
| WO | WO 95/34298 | 12/1995 |
| WO | WO 96/00055 | 1/1996 |
| WO | WO 96/19233 | 6/1996 |
| WO | WO 97/09973 | 3/1997 |
| WO | WO 97/21445 | 6/1997 |
| WO | WO 98/38996 | 9/1998 |
| WO | WO 98/41171 | 9/1998 |
| WO | WO 98/47890 | 10/1998 |
| WO | WO 00/01379 | 1/2000 |
| WO | WO 00/03705 | 1/2000 |
| WO | WO 00/23061 | 4/2000 |
| WO | WO 00/23062 | 4/2000 |
| WO | WO 00/23066 | 4/2000 |
| WO | WO 00/23072 | 4/2000 |
| WO | WO 00/25745 | 5/2000 |
| WO | WO 00/35433 | 6/2000 |
| WO | WO 00/69255 | 11/2000 |
| WO | WO 01/07050 A1 | 1/2001 |
| WO | WO 01/41550 A2 | 6/2001 |
| WO | WO 01/82914 A2 | 11/2001 |
| WO | WO 02/05815 A1 | 1/2002 |
| WO | WO 02/24191 A1 | 3/2002 |
| WO | WO 02/09702 | 7/2002 |

OTHER PUBLICATIONS

Antcliff et al., "The maintenance of per-operative mydriasis in phacoemulsification with topical diclofenac sodium," *Eye* 11:389-391 (1997).

Liou, Shiow-Wen, et al., "The Effects of Intracameral Adrenaline Infusion on Pupil Size, Pulse Rate, and Blood Pressure During Phacoemulsification," *J Ocular Pharmacol Ther* 14(4):357-361 (1998).

Gimbel, "The effect of treatment with topical nonsteroidal anti-inflammatory drugs with and without intraoperative epinephrine on the maintenance of mydriasis during cataract surgery," *Ophthalmology* 96(5):585-588 (1989).

Shimada, H., et al., "Effects of Flubiprofen on Extracapsular Cataract Extraction," *Journal of the Eye* 4(5):719-722 (1987). Japanese language.

Shimada, H., et al., "Effects of Flubiprofen on Extracapsular Cataract Extraction," *Journal of the Eye* 4(5):719-722 (1987). English Translated copy.

Titcomb, "Revision of Pharmacology," www.optometry.co.uk 25-34 (2002).

Zimm, Jeffrey L., et al., "Effects of topical suprofen and flurbiprofen on the miosis produced by anterior chamber irrigation with cholinergic agonists," *J Cataract Refract Surg* 17:790-793 (1991).

Snyder, R.W., et al., "Acular as a single agent for use an an antimiotic and anti-inflammatory in cataract surgery," *J Cataract Refract Surg* 26(8): 1225-1227 (2000).

Shimoda, H., et al., "Effects of an Anti-prostaglandin Agent Added to the Irrigation Solution on Damage to the Anterior Segment in Monkey Eyes Induced by Pars Plana Vitrectomy," *Acta Soc Ophthalmol Jpn* 93:823-829 (1989). Japanese language with English abstract.

Miyake et al., "Latanoprost Accelerates Disruption of the Blood-Aqueous Barrier and the Incidence of Agiographic Cystoid Macular Edema in Early Postoperative Pseudophakias," *Arch Ophthalmol* 117:34-40 (1999).

Miyake et al., "Enhanced Disruption of the Blood-Aqueous Barrier and the Incidence of Angiographic Cystoid Macular Edema by Topical Timolol and Its Preservative in Early Postoperative Pseudophakia," *Arch Ophthalmol* 119:387-394 (2001).

Fichman, "Anesthesia and preoperative and postoperative medications," *Current Opinion in Ophthalmology* 7:17-20 (1996).

Alcon Laboratories, "The Worldwide Winner TobraDex," Internet Publication, www.alconlabs,com/us/aj/products/RxTher/TobraDexPro.jhtml (Jun. 3, 2003).

Heier, J., et al., "Ketorolac tromethamine 0.5% ophthalmic solution in the treatment of moderate to severe ocular inflammation after cataract surgery: a randomized, vehicle-controlled clinical trial," *Am J Ophthalmol* 127(3):253-9 (1999).

Alcon Laboratories, "Sterile Intraocular Irrigating Solution," Internet Publication, www.alconlabs.com/ca_en/aj/products/bss-pml.jhtml (Jun. 26, 2003).

Wang, R.F., et al., "Effect of Oxymetazoline on Aqueous Humor Dynamics and Ocular Blood Flow in Monkeys and Rabbits," *Arch Ophthalmol* 111:535-8 (1993).

Chu, Teh-Ching, et al., "Oxymetazoline: Potential Mechanisms of Inhibitory Effects on Aqueous Humor Dynamics," *Pharmacology* 53:259-270 (1996).

Patil, Popat N., et al., "Antimuscarinic Action of Oxymetazoline on Human Intraocular Muscles," *Journal of Ocular Pharmacology and Therapeutics* 20(4):328-332 (2004).

Flach, A.J., et al., "Effectiveness of ketorolac tromethamine 0.5% ophthalmic solution for chronic aphakic and pseudophakic cystoid macular edema," *Am J Ophthalmol* 103(4):479-86 (1987).

Anderson, Janet A., et al., "Multiple Dosing Increases the Ocular Bioavailability of Topically Administered Flurbiprofen," *Arch Ophthalmol* 106:1107-1109 (1988).

(56) References Cited

OTHER PUBLICATIONS

Ishikawa, H., et al., "Comparison of post-junctional alpha-adrenoceptors in iris dilator muscle of humans, and albino and pigmented rabbits," *Naunyn Schmeidebergs Arch Pharmacol* 354(6):765-72 (1996).
Lion, Shiow-Wen, et al., "Maintenance of Mydriasis with One Bolus of Epinephrine Injection During Phacoemulsification," *J Ocular Pharmacol Ther* 17(3):249-253 (2001).
Lundberg, Björn, M.D., et al., "Intracameral mydriatics in phacoemulsification cataract surgery," *J Cataract Refract Surg* 29:2366-2371 (2003).
Flach, Allan J., "Cyclo-oxygenase Inhibitors in Ophthalmology," *Survey of Ophthalmology* 36(4):259-284 (1992).
Flach, A.J., et al., "The effect of ketorolac tromethamine solution 0.5% in reducing postoperative inflammation after cataract extraction and intraocular lens implantation," *Ophthalmology* 95(9):1279-84 (1988).
Flach, Allan, J., "Corneal Melts Associated with Topically Applied Nonsteroidal Anti-Inflammatory Drugs," *Tr Am Opth* 99:205-212 (2001).
"The Pocket Oxford American Dictionary of Current English," Oxford University Press, New York, p. 418 (2002).
"The Bantam Medical Dictionary," Laurence Urdang Associates Ltd., Bantam Books, New York, p. 17 (1981).
Gills, J.P., "Intraocular irrigating solutions with cataract surgery," *Atlas of Cataract Surgery*, Masket, Samuel MD and Crandall, Alan S MD, eds. Chapter 3, Martin Dunitz Publisher (1999).
Gills, J.P., et al., Comment on "Bacterial endophthalmitis prophylaxis," *Ophthalmology* 110(8):1668 (2003).
Gills, J.P., et al., "Effect of intracameral triamcinolene to control inflammation following cataract surgery," *J Cataract Refract Surg* 31(8):1670-1 (2005).
Gills, J.P., "My Method of Extracapsular Cataract Extraction With Implantation of a Posterior Chamber Intraocular Lens," *Ophthalmic Surgery* 16(6):386-392 (1985).
Hirowatari, Takeo, et al., "Evaluation of a New Preoperative Opthalmic Solution," *Can J Ophthalmol* 40:58-62 (2005).
Snyder, R.W., et al., "Acular as a single agent for use an an antimiotic and anti-inflammatory in cataract surgery," *J Cataract Refract Surg* 26:1225-127 (2000).
Srinivasan, M.S., et al., "Topical ketorolac tromethamine 0.5% versus diclofenac sodium 0.1% to inhibit miosis during cataract surgery," *J Cataract Refract Surg* 28:517-520 (2002).
*Taber's Cyclopedic Medical Dictionary*, 19th Edition, F.A. Davis Company, Philadelphia, pp. 1131-1132 (2003).
Eleftheriadis, H., et al., "Corneal toxicity secondary to inadvertent use of benzalkonium chloride preserved viscoelastic material in cataract surgery," *British Journal of Ophthalmology* 86:299-305 (2002).
Zaczek, A., et al., "The effect of phenylephrine on pain and flare intensity in eyes with uvitis," *Acta Ophthalmologica Scandinavica* 78:516-518 (2000).
Online Merck Manual Home Edition articles entitled, "Inflammation," "Blepharitis," "Dacrocystitis," "Infections," "Gout," "Pseudogout," "Sinusitis," "Pharyngitis," "Reiter's Syndrome," "Tongue Disorders," "Meningitis," "Viral Infections," "Hemrroids," "Urethritis," "Episcleritis," "Conjunctivitis," and "Rheumatoid Arthritis," www.merck.com/mmhe/print/sec20/ch236/ch236d.html, 51 pages, accessed Mar. 2007 (2003).
Medline Plus, Medical Encyclopedia: Neuroretinitis, Definition of "Neuroretinitis", www.nlm.nih.gov/medlineplus/ency/article/002268.htm, accessed Mar. 2007, (2005).
Kuby, J., "Immunology," Third Edition, W.H. Freeman and Company, New York, pp. 67 and 365-378, (1997).
Chaudhary, K.P., et al., "Preoperative Topical Flubiprofen—Na$^+$ in Extracapsular Lens Extraction Role in Maintaining Intraoperative Pupillary Dilation," *Ind J Opthal.* 40(4):109-114 (1992).
Arshinoff, S.A., et al., "Pharmacotherapy of Photorefractive Keratectomy," *J Cataract Refract Surg* 22:1037-1044 (1996).
Volpe, N, et al., "Single Dose Ondansetron for Prevention of Postoperative Nausea and Vomiting," *Drug Invest* 8(2):67-72 (1994).

Cherry, P.M.H., et al., "The Treatment of Pain Following Excimer Laser Photorefractive Keratectomy: Additive Effect of Local Anesthetic Drops, Topical Diclofenac, and Bandage Soft Contact," *Opthalmic Surg Lasers* 27:S477-S480 (1996).
Gurbaxani, A., et al., "Intracameral phenylephrine to prevent floppy iris syndrome during cataract surgery in patients on tamsulosin," *Eye* 21:331-332 (2007).
Goyal, R., et al., "Randomised Controlled Trial of Ketorolac in the Management of Corneal Abrasions," *Acta Ophthalmol, Scand.* 79:177-179 (2001).
Arshinoff, S., et al., "Use of Topical Nonsteroidal Anti-Inflammatory Drugs in Excimer Laser Photorefractive Keratectomy," *J Cataract Refract Surg* 20:216-222 (1994).
Busse, W., et al., "A Multicenter, Double-Blind, Randomized, Placebo-Controlled Trial Comparing the Efficacy and Tolerability of Levocabastine-Oxymetazoline Nasal Spray with Levocabastine and Oxymetazoline Alone in the Symptomatic Treatment of Seasonal Allergic Rhinitis," *American Journal of Rhinology* 10(2):105-111 (1996).
Quiroz, C., et al., "N.F.12: A New Topical Solution for External Eye Disease," *American Journal of Ophthalmology* 41(6):1020-1024 (1956).
Grahn, B., et al., "Diagnostic Ophthalmology," *Can Vet J* 35:730-731 (1994).
Angra, S.K., et al., "Safe and Effective Management of Vernal Keratoconjunctivitis (VKC): A Double Blind Clinical Study," *Ann Natl Acad Med Sci (India)* 25(1):9-12 (1989).
Batra D., et al., "Patterns of Responses to Alternative Medicines in Controlling Allergic Conjunctivitis," *Ind. J. Ophthal* 36(1):17-21 (1998).
Matsuda, M., et al., "The Addition of Oxidized Glutathione to Intraocular Irrigating Solutions to Prevent Corneal Endothelial Damage During Intraocular Surgery," *Folia Ophthalmol Jpn* 41:1093-1098 (1990). Japanese original and English translated copy.
Nishide, T., et al., "Topical Anesthesia with Additional Intracameral Irrigation of 0.2% Lidocaine during Cataract Surgery in High Myopic Eyes," *Jpn J Clin Ophthalmol* 53(5):921-922 (1999). Japanese original and English translated copy.
Kinoshita, A., "Mydriatic Efficacy of Irrigated Phenylephrine during Extracapsular Cataract Surgery," *Folia Ophthalmol Jpn* 40:1730-1733 (1989). Japanese original and English translated copy.
Tsuchisaka, H., "How to Use Surgical Adjuvents and Drugs in IOL Implantation," *Journal of the Eye* 4(6):755-759 (1987). Japanese original and English translated copy.
Lacy, C. et al, "Drug Information Handbook," Lexi-Comp, Inc. Cleveland, Ohio, pp. 497 and 717-719, (1993).
Katsura, Hiroshi, "How to Use Local Anesthetic," *Eye Clinic* 27:1055-1060 (1985). Japanese language.
Katsura, Hiroshi, "How to Use Local Anesthetic," *Eye Clinic* 27:1055-1060 (1985). English language.
Sandoval, H.P., et al., "A review of the use of ketorolac tromethamine 0.4% in the treatment of post-surgical inflammation following cataract and refractive surgery," *Clin Ophthalmol* 1(4):367-71 (2007).
Suleiman, Y.M., et al., "Comparison of ketorolac tromethamine and prednisolone acetate in preventing surgically induced miosis during cataract surgery," *Sultan Qaboos Univ Med J* 10(1):57-63 (2010).
Adrenalin [package insert]. JPH Pharmaceuticals, LLC, Rochester, MI; 2004.
Arshinoff, S.A., et al. (2009). The pharmacotherapy of cataract surgery. In *Ophthalmology* (M. Yanoff and J.S. Duker, Eds.) Third Edition. (pp. 434-440). Elsevier.
Batenburg, W., et al., "Carvedilol-induced antagonism of angiotensin II: a matter of $\alpha_1$-adrenoceptor blockade," *Journal of Hypertension* 24:1355-1363 (2006).
Behndig, A., et al., "Mydriatic response to different concentrations of intercameral phenylephrine in humans," *J Cataract Refract* 36:1682-1686 (2010).
Bhattacharjee, A.K., et al., "MMP-9 and EBA immunoreactivity after papaverine mediated opening of the blood-brain barrier," *NeuroReport* 13:2217-2221 (2002).
Fine, I.H., et al. (2009). Phacoemulsification in the presence of a small pupil. In *Cataract Surgery: Expert Consult* (R. Steinert, Ed.) Third Edition (pp. 245-258). Elsevier.

(56) References Cited

OTHER PUBLICATIONS

Flach, A.J., et al., "Improvement in visual acuity in chronic aphakic and pseudophakic cystoid macular edema after treatment with topical 0.5% ketorolac tromethamine," *Am J Ophthalmol* 112:514-519 (1991).
Guzek, J.P., et al., "Risk factors for intraoperative complications in 1000 extracapsular cataract cases," *Ophthalmology* 94:461-466 (1987).
Ho, T., et al., "Maximal mydriasis evaluation in cataract surgery," *J Cataract Refract Surg* 18:375-379 (1992).
Holló, G. "The side effects of the prostaglandin analogues," *Expert Opin Drug Saf* 6(1):45-52 (2007).
Kozlowska, H., et al., "Ligands at $\beta_2$-, $\beta_3$-, and the low-affinity state of $\beta_1$-adrenoceptors block the $\alpha_1$-adrenoceptor-mediated constriction in human pulmonary and rat mesenteric arteries," *J Cardiovasc Pharmacol* 46(1):76-82 (2005).
Mamalis, N. (2009). Toxic anterior segment syndrome. In *Cataract Surgery: Expert Consult* (R. Steinert, Ed.) Third Edition. (pp. 589-594). Elsevier.
Moroi, S.E., et al. (2001). Ocular pharmacology. In *Goodman & Gilman's The Pharmacological Basis of Therapeutics* (J.G. Hardman and L.E. Limbird, Eds.) Tenth Edition. (pp. 1821-1848). McGraw-Hill.
Nakamura, S., et al., "Evaluation of $\alpha_1$-adrenoceptors in the rabbit iris: pharmacological characterization and expression of mRNA," *Br J Pharmacol* 127:1367-1374 (1999).
Narendran, N., et al., "The cataract national dataset electronic multicenter audit of 55 567 operations: risk stratification for posterior capsule rupture and vitreous loss," *Eye* 23:31-37 (2009).
Neuhann, T.F. et al. (2009). Capsulorrhexis. In *Cataract Surgery: Expert Consult* (R. Steinert, Ed.) Third Edition. (pp. 163-171). Elsevier.
Radi, Z.A., et al., "The pathophysiologic role of cyclooxygenases in the eye," *J Ocular Pharmacol Ther* 24(2):141-151 (2008).
Rutar, T., et al., "Risk factors for intraoperative complications in resident-performed phasoemulsificatin surgery," *Ophthalmology* 116:431-436 (2009).
Schalnus, R. "Topical nonsteroidal anti-inflammatory therapy in ophthalmology," *Ophthalmologica* 217:89-98 (2003).
Waitzman, M.B. "Prostaglandins and the eye," *Metabolic, Pediatric and Systemic Ophthalmology* 6:17-26 (1982).
Menapace, R. (2005). Prevention of posterior capsule opacification. In *Cataract and Refractive Surgery* (T. Kohnen and D. Koch, Eds.) (pp. 101-122), Springer.
Acular [package insert]. Allergan, Inc., Irvine, CA; 2004.
Srinivasan, M., et al., "Sodium bicarbonate—an alternative to hyaluronidase in ocular anaesthesia for cataract surgery," *Indian Journal of Ophthalmology* 48(4):285-89 (2000).
Solomon, K.D., et al., "Topical 0.5% ketorolac vs 0.03% flurbiprofen for inhibition of miosis during cataract surgery," *Arch Opthalmol* 115:1119-1122 (1997).
Gills, J.P., "Injectable Prostaglandins Inhibitors Prior to Cataract Surgery," *J Cataract Refract* 13:459-460 (1987).
Yuen, V.H., et al., "Comparison of three modified lidocaine solutions for use in eyelid anesthesia," *Ophthalmic Plastic and Reconsturctie Surgery* 15(2):143-147 (1999).
Krohn, J., et al., "Retrobulbar anesthesia with and without hyaluronidase in extracapsular cataract surgery," *Acta Opthalmologica* 71:791-795 (1993).
Keates, R.H., et al., "Clinical trial of flurbiprofen to maintain pupillary dilation during cataract surgery,", *Ann.Ophthalmol.* 16(10):919-921 (1984).
Gills, J.P., et al. "Pharmacodynamics of Cataract Surgery" & "Strategies for Applying State of the Art Techniques," *Cataract Surgery The State of the Art* Chapters 3 & 18:19-26, 229-240 (1998).
Keates, R.H., et al., "The effect of topical indomethacin ophthalmic solution in maintaining mydriasis during cataract surgery," *Ann. Ophthalmol.* 16(12)1116-1121 (1984).

Papa, V., et al., "Topical naproxen sodium for inhibition of miosis during cataract surgery. Prospective, randomized clinical trials," *Eye* 16(3):292-296 (2002).
Lundberg, B. et al., "Intracameral Mydriatics in Phacoemulsification Surgery Obviate the Need for Epinephrine Irrigation," *Acta Ophthalmol. Scand.* 85:546-550 (2007).
Allergan. (2011). *Acuvail®(ketorolac tromethamine ophthalmic solution) 0.45%*. Irvine, CA. (Package Insert).
Allergan. (2011). *Acular—ketorolac tromethamine solution/drops*. Irvine, CA. (Package Insert).
Allergan. (2001). *Acular®(ketorolac tromethamine ophthalmic solution) 0.5% Sterile*. Irvine, CA. (Package Insert).
Bedford Laboratories. (2008) *Ketorolac Tromethamine (ketorolac tromethamine) Injection, Solution*. Retrieved from http://dailymed.nlm.nih.gov/dailymed/archives/fdaDrugInfo.cfm?archivedid=8730. (Package Insert).
Falcon Pharmaceuticals, Ltd., et al. *Phenylephrine Hydrochloride Ophthalmic Solution, 2.5%*. Fort Worth, TX. (Package Insert).
Phenylephrine Hydrochloride, (2012), In *Medicines Support Unit for Optometrists*. Retrieved from http://www.med-support.org.uk/IntegratedCRD.nsf/b73d388be6b449968025768c005313. (Package Insert).
InterMed Medical Ltd. (2005). Neo-Synephrine® Phenylephrine Hydrochloride 1% Injection. In *Information for Health Professionals Data Sheet*. Retreived from file:///H|/OMS302/Commercial PE and KT products/Neo-Synephrine product info.htm.
Hirowatari, T., et a., "Availability of TPD ophthalmic Solution (Mixture of Mydria-P Solution, Neosynesin Kowa Solution, and Diclod Solution)," *New Ophthalmology* 19(1):107-109 (2002). Japanese Language.
Hirowatari, T., et a., "Availability of TPD ophthalmic Solution (Mixture of Mydria-P Solution, Neosynesin Kowa Solution, and Diclod Solution)," *New Ophthalmology* 19(1):107-109 (2002), English Translation.
Ogawa, T., et al., "Effects of Pre-installed Mydriatics on the Intraocular Concentration and Wnti-inflammatory Action of Topical 0.1% Pranoprofen (3)—Study on Permeability Factor," *Journal of Japanese Ophthalmological Society* 96(11):1379-1386 (1992). Japanese Language.
Ogawa, T., et al., "Effects of Pre-installed Mydriatics on the Intraocular Concentration and Wnti-inflammatory Action of Topical 0.1% Pranoprofen (3)—Study on Permeability Factor," *Journal of Japanese Ophthalmological Society* 96(11):1379-1386 (1992). English Translation.
Kim, S.J., et al., "Nonsteroidal anti-inflammatory drugs in ophthalmology," *Surv. Ophthalmol.* 55(2):108-133 (2010).
Lindstrom, R.L., et al., "Intracameral phenylephrine and ketorolac injection (OMS302) for maintenance of intraoperative pupil diameter and reduction of postoperative pain in intraocular lens replacement with phacoemulsification," *Clin.Ophthalmol.* 8:1735-1744 (2014).
DeRuiter, Principals of Drug Action 2 at 4 (Fall, 2002), accessed Apr. 26, 2015 at www.auburn.edu/~deruija/nsaids_2002.pdf.
Goodman & Gilman's, The Pharmacologic Basis of Therapeutics, 10th edition, pp. 145-146, 216-218, 687-692 (2001).
Ansari, H.R., et al., "Effects of prostaglandin F2alpha, latanoprost and carbachol on phosphoinositide turnover, MAP kinases, myosin light chain phosphorylation and contraction and functional existence and expression of FP receptors in bovine iris sphincter," *Exp. Eye Res.* 78(2):285-296 (2004).
Zanetti, F.R., "Effect of preoperative use of topical prednisolone acetate, ketorolac tromethamine, nepafenac and placebo, on the maintenance of intraoperative mydriasis during cataract surgery: a randomized trial," *Indian J. Ophthalmol.* 60(4):277-281 (2012).
Keulen-de Vos, H.C., et al., "Effect of indomethacin in preventing surgically induced miosis," *Br. J. Ophthalmol.* 67(2):94-96 (1983).
Guzinska, M., et al.., "[The effect of diclofenac sodium and indomethacin used locally for maintenance of pupiliary dilatation during cataract surgery]," *Kiln.Oczna* 100(1):19-22 (1998). English Language Abstract Included.

(56) References Cited

OTHER PUBLICATIONS

Guimaraes-Filho, S.R., et al., "Comparison of the anti-inflammatory effects of topically applied aspirin and indomethacin following photocoagulation of the rabbit iris," *Braz.J.Med.Biol.Res.* 25(1):67-73 (1992).

Ahlquist, RP, "Present State of Alpha- and Beta-Adrenergic Drugs I. The Adrenergic Receptor," *Am Heart J.* 92(5):661-4 (1976).

Gupta, V.P., et al., "Ketorolac tromethamine in the maintenance of intraoperative mydriasis," *Ophthalmic Surg.Lasers* 28(9):731-738 (1997).

Database WPI Week 200256, *Derwent Publications Ltd.*, London, GB: AN 2002-523513 & JP 2002 161032 A, *Tasisho Pharm Co. Ltd*, Jun. 4, 2002. Abstract Only.

Database WPI Week 200239; *Derwent Publications Ltd.*, London, GB; AN 2002-362397 XP002478749 & WO 02/24191 A, *Yong Guang Pharm Co Ltd*, Mar. 28, 2002. Abstract Only.

Gills, James, "Cataract Surgery Pharmacology—A leading surgeon shares several ways he's improved his medication protocol and raised his standard of care," *Opthalmology Management*, Sep. 2001. http://www.ophthalmologymanagement.com/articleviewer.aspx?articleid=85211.

OPHTHALMOLOGIC IRRIGATION SOLUTIONS AND METHOD

I. CROSS REFERENCE TO RELATED APPLICATIONS

The present invention is a continuation of currently pending U.S. patent application Ser. No. 13/420,440, filed Mar. 14, 2012, which is a continuation of U.S. patent application Ser. No. 12/799,981 filed May 5, 2010, now U.S. Pat. No. 8,173,707, which is a continuation of U.S. patent application Ser. No. 10/630,626 filed Jul. 30, 2003, now abandoned, which claims the benefit of the filing date of U.S. Provisional Application No. 60/399,899, filed Jul. 30, 2002, priority from the filing dates of which are hereby claimed under 35 U.S.C. §120.

II. FIELD OF THE INVENTION

The present invention relates to surgical irrigation solutions and methods, and particularly to irrigation solutions for use during ophthalmologic procedures.

III. BACKGROUND OF THE INVENTION

Ophthalmologic surgery typically requires the use of a physiologic irrigation solution to protect and maintain the physiological integrity of intraocular tissues. Examples of ophthalmologic surgical procedures usually requiring irrigation solutions are cataract operations, corneal transplant operations, vitreoretinal operations and trabeculectomy operations for glaucoma.

Solutions that have been used in ophthalmologic surgical irrigation include normal saline, lactated Ringer's solution and Hartmann's lactated Ringer's solution, but these are not optimal due to potential unfavorable corneal and endothelial effects. Other aqueous solutions that include agents such as electrolytes, buffering agents for pH adjustment, glutathione and/or energy sources such as dextrose, better protect the tissues of the eye, but do not address other physiologic processes associated with surgery. One commonly used solution for ophthalmologic irrigation is a two part buffered electrolyte and glutathione solution disclosed in U.S. Pat. No. 4,550,022 to Garabedian et al., the disclosure of which is hereby expressly incorporated by reference. The two parts of this solution are mixed just prior to administration to ensure stability. These solutions are formulated with a goal of maintaining the health of ocular tissues during surgery.

Modifications of conventional aqueous irrigation solutions by the addition of therapeutic agents have been proposed. For example, U.S. Pat. No. 5,523,316 to Gan et al. discloses the addition of one or more agents for controlling intraocular pressure to irrigation solutions. Specific examples of agents for controlling intraocular pressure disclosed in the Gan et al patent, all disclosure of which is hereby incorporated by reference, are beta-blockers (i.e., beta adrenergic receptor antagonists) and alpha-2 adrenergic receptor agonists. Reference is also made to muscarinic agonists, carbonic anhydrase inhibitors, angiostatic steroids and prostaglandins as classes of drugs that control intraocular pressure. Only agents intended for the control of intraocular pressure are envisioned.

Another example of a modified solution is disclosed in International PCT Application WO 94/08602 in the name of inventors Gan et al., the disclosure of which is hereby incorporated by reference. This application discloses the inclusion of a mydriatic agent, such as epinephrine, in ocular irrigation solutions. Still another example is provided by International PCT Application WO 95/16435 in the name of inventors Cagle et al., which discloses the inclusion of non-steroidal anti-inflammatory drugs (NSAIDs) in an ophthalmologic irrigation solution.

A topical ophthalmologic solution is disclosed in U.S. Pat. No. 5,811,446 to Thomas that includes histidine, and which may include at least one other active agent such as an anti-glaucoma agent, such as timolol or phenylephrine, a steroid or an NSAID. This reference teaches application of the composition to limit the inflammation associated with ophthalmic procedures. The solution is administered by a dropper into the cul-de-sac of the eye.

U.S. Pat. No. 5,624,893 to Yanni includes compositions including a wound healing agent, such as a steroid or a growth factor, and/or a pain mediator, such as an NSAID, a bradykinin antagonist, or a neurokinin-1 antagonist. The compositions are intended for the treatment and prevention of corneal haze associated with laser irradiation and photoablation.

Although many topically applied agents are available or have been proposed to treat ocular inflammation, produce mydriasis (typically necessary to perform many types of ophthalmologic surgery), or to control intraocular pressure, no previous attempt has been made to combine these agents for use in a perioperative ocular irrigation solution that is delivered in such a way so as to provide a constant, controlled delivery of multiple therapeutic agents, that act on multiple molecular targets to address multiple physiologic functions, to the tissues of the eye throughout a procedure.

Various methods of ocular drug delivery are conventionally employed, each of which has limitations. These limitations may include corneal and conjuctival toxicity, tissue injury, globe perforation, optic nerve trauma, central retinal artery and/or vein occlusion, direct retinal drug toxicity, and systemic side effects. For example, topical medications applied drop-wise are frequently impeded in reaching a targeted ocular site due to the eye's natural protective surface. In many situations, a rather small percentage of the medication applied to the surface of the eye will actually reach the desired therapeutic site of action.

One difficulty in ocular drug delivery during surgical procedures is to achieve the desired therapeutic concentration levels with the proper temporal control. The most desired pharmacokinetic effect is to be able to rapidly achieve a therapeutic concentration range and subsequently maintain the drug concentration at a constant level. This is not achieved by conventional methods of ocular drug delivery. The challenge of achieving similar pharmacokinetic profiles is substantially compounded when it is desirable to simultaneously deliver more than one drug. A unique group of factors affect the ability of a drug to penetrate the corneal epithelia, including the size of the molecule, its chemical structure and its solubility characteristics.

To achieve sufficient concentration of drug delivered to the back of the eye, drugs are frequently administered systemically at very high doses. These levels are necessary to overcome the blood-retina barrier that protects the back of the eye from selected drug molecules coming from the blood stream. For surgical procedures, injectable drug solutions are sometimes injected directly into the back of the eye. Subconjuctival and peribulbar periocular injections are used when higher local concentrations are needed and when drugs with poor penetration characteristics need to be delivered. Intracameral injections directly into the anterior chamber are used in cataract surgery. While intracameral injection provides a prompt method of achieving a concentration, it can be associated with corneal toxicity. However, this method suffers from the fact that these drugs are quickly removed by the eye's natural circulatory process. Thus, injectable solutions rapidly lose their therapeutic benefit, often necessitating frequent, large dose injections that can carry toxicity risks. Sustained release formulations, such as viscoelastic gels containing microcapsules, may be injected intraocularly for a longer duration of action. However, there may be some delay in reaching a local therapeutic concentration of drug. Hence, there exists a need for controlled methods of ocular delivery during ophthalmologic procedures.

IV. SUMMARY OF THE INVENTION

The present invention provides solutions for local ocular delivery of multiple active agents that act on a plurality of differing molecular targets to perioperatively inhibit inflammation, inhibit pain, effect mydriasis (dilation of the pupil), and/or to decrease intraocular pressure. The solutions and methods of the present invention use at least first and second therapeutic agents that are selected from the physiologic functional classes of anti-inflammatory agents, analgesic agents, mydriatic agents and agents for decreasing intraocular pressure ("IOP reducing agents"), the second agent providing at least one physiologic function different than a function or functions provided by the first agent. The solutions are preferably applied by continuous irrigation of ocular tissues at the site of surgery during a majority of the operative procedure.

Solutions of this aspect of the present invention may include: (a) one or more anti-inflammatory agents in combination with one or more analgesic agents, and optionally may also include one or more IOP reducing agents and/or mydriatic agents; (b) one or more anti-inflammatory agents in combination with one or more IOP reducing agents, and optionally one or more analgesic and/or mydriatic agents; (c) one or more anti-inflammatory agents in combination with one or more mydriatic agents, and optionally one or more analgesic agents and/or IOP reducing agents; (d) one or more analgesic agents in combination with one or more IOP reducing agents, and optionally one or more anti-inflammatory agents and/or mydriatic agents; (e) one or more analgesic agents in combination with one or more mydriatic agents, and optionally one or more anti-inflammatory agents and/or IOP reducing agents; or (f) one or more mydriatic agents in combination with one or more IOP reducing agents, and optionally one or more anti-inflammatory and/or analgesic agents.

The present invention provides a solution constituting a mixture of multiple agents in low concentrations directed at inhibiting locally the mediators of pain, inflammation, reducing intraocular pressure and/or causing mydriasis, in a physiologic electrolyte carrier fluid. The invention also provides a method for perioperative delivery of the irrigation solution containing these agents directly to a surgical site, where it works locally at the receptor and enzyme levels to preemptively limit pain and inflammation, reduce intraocular pressure and/or cause mydriasis, at the site. Due to the local perioperative delivery method of the present invention, a desired therapeutic effect can be nearly instantaneously achieved with lower doses of agents than are necessary when employing systemic methods of delivery (e.g., intravenous, intramuscular, subcutaneous and oral) or by injection. When applied by continuous irrigation during a majority of the procedure, in accordance with a preferred aspect of the invention, concentrations of agents utilized may be lower than if the agents were applied drop-wise in a single application or by intraocular injection.

The present invention has several advantages over other types of compositions and methods for delivery of active agents during intraocular surgery. Liquid compositions for topical drop-wise instillation of a pharmaceutical agent to the eye do not always provide an accurate method for delivering a defined dosage, because portions of the drop are either blinked away or drain away during administration. Furthermore, subsequent use of a normal irrigation solution can be anticipated to effectively dilute and remove a dose delivered drop-wise delivered to the eye during an intraocular or topical ophthalmologic procedure before the start of the surgical procedure, thereby reducing the therapeutic efficacy of the agent.

In addition, the increased time over which the drugs can be delivered in accordance with the present invention via irrigation during an intraocular or topical ophthalmologic procedure allows a lower concentration of the drugs to be used in the irrigation solution, which reduces the risk of ocular toxicity. Due to pharmacokinetic considerations, doses of agents delivered only pre-operatively will exhibit a variable concentration and efficacy as a function of time, reaching a peak of effectiveness some time after the initial application, then subsequently declining in efficacy due to a progressively decreasing concentration. The particular pharmacokinetic parameters after topical instillation of a drug will vary for each drug depending on the solubility characteristics of the agent, the vehicle composition, and the pH, osmolality, tonicity and viscosity of the formulation. One advantage of the invention is that the irrigation solutions provided maintain a constant concentration of active agents at the ocular surgery site, thereby maintaining a constant therapeutic effect.

The present invention provides for controlled, site-specific drug delivery to the eye for the dual purposes of increasing efficacy and decreasing side effects of ocular therapy. A therapeutic concentration range is rapidly achieved, and is subsequently maintained at an effectively constant level during the period of irrigation.

The present invention also provides a method for manufacturing a medicament compounded as a dilute irrigation solution for use in continuously irrigating an operative site or wound during an operative procedure. The method entails dissolving in a physiologic electrolyte carrier fluid a plurality of analgesic agents, anti-inflammatory agents, mydriatic agents, and/or agents that decrease intraocular pressure ("IOP reducing agents"), each agent included at a concentration of preferably no more than 100,000 nanomolar, and more preferably no more than 10,000 nanomolar, except for local anesthetics, which may be applied at a concentration of no more than 100,000,000 nanomolar, preferably no more than 10,000,000 nanomolar, more preferably no more than 1,000,000 nanomolar, and still more preferably no more than 100,000 nanomolar.

The method of the present invention provides for the delivery of a dilute combination of multiple receptor antagonists and agonists and enzyme inhibitors and activators directly to a wound or operative or procedural site of the eye, during surgical, therapeutic or diagnostic procedures for the inhibition of pain and inflammation, reduction or control of intraocular pressure, and/or the promotion of mydriasis. Because the active ingredients in the solution are being locally applied directly to the ocular tissues in a continuous fashion during the procedure, the drugs may be used efficaciously at extremely low doses relative to those doses required for therapeutic effect when the same drugs are delivered systemically (e.g., orally, intramuscularly, subcutaneously or intravenously), or in a single application such as drop-wise or by intraocular injection.

As used herein, the term "local" encompasses application of a drug in and around a wound or other operative or procedural site, and excludes oral, subcutaneous, intravenous and intramuscular administration. As used herein throughout, the term "irrigation" is intended to mean the flushing of a wound or anatomic structure with a stream of liquid. The term "continuous" as used herein encompasses uninterrupted application, repeated application at frequent intervals at a frequency sufficient to substantially maintain a predetermined therapeutic local concentration of the applied agents, and applications which are uninterrupted except for brief cessations such as to permit the introduction of other drugs or procedural equipment or due to operative technique, such that a substantially constant predetermined therapeutic local concentration is maintained locally at the wound or operative site.

As used herein, the term "wound", unless otherwise specified, is intended to include surgical wounds, operative/interventional sites and traumatic wounds.

As used herein, the terms "operative" and "procedural", unless otherwise specified, are each intended to include surgical, therapeutic and diagnostic procedures.

The irrigation solution including selected therapeutic agents is locally and perioperatively applied to ocular tissues of the operative site, e.g., intraocularly for intraocular procedures and to the exterior of the eye for superficial procedures. As used herein, the term "perioperative" encompasses application intraprocedurally, pre- and intraprocedurally, intra- and postprocedurally, and pre-, intra- and postprocedurally. Preferably, the solution is applied preprocedurally and/or postprocedurally as well as intraprocedurally. The irrigation solution is most preferably applied to the wound or surgical site prior to the initiation of the procedure, or before substantial tissue trauma, and continuously throughout the duration of the procedure, to preemptively block pain and inflammation, inhibit intraocular pressure increases, and/or cause mydriasis. In a preferred aspect of the invention, continuous irrigation is delivered throughout a substantial portion of the procedure, before and during the majority of operative trauma, and/or during the period when mydriasis may be required and/or control of intraocular pressure may be required.

The advantages of low dose application of agents by irrigation with the methods and solutions of the present invention are three-fold. Systemic side effects that often limit the usefulness of these agents are avoided. Additionally, the agents selected for particular applications in the solutions of the present invention are highly specific with regard to the mediators on which they work. This specificity is maintained by the low dosages utilized. Finally, the cost of these active agents per operative procedure is low.

More particularly: (1) local administration guarantees a known concentration at the target site, regardless of interpatient variability in metabolism, blood flow, etc.; (2) because of the direct mode of delivery, a therapeutic concentration is obtained nearly instantaneously and, thus, improved dosage control is provided; and (3) local administration of the active agents directly to a wound or operative site also substantially reduces degradation of the agents through extracellular processes, e.g., first- and second-pass metabolism, that would otherwise occur if the agents were given systemically (e.g., orally, intravenously, subcutaneously or intramuscularly). This is particularly true for those active agents that are peptides, which are metabolized rapidly. Thus, local administration permits the use of compounds or agents which otherwise could not be employed therapeutically. Local, continuous delivery to the wound or operative site minimizes drug degradation or metabolism while also providing for the continuous replacement of that portion of the agent that may be degraded, to ensure that a local therapeutic concentration, sufficient to maintain receptor occupancy, is maintained throughout the duration of the operative procedure.

Local administration of the solution perioperatively throughout a surgical procedure in accordance with the present invention produces preemptive analgesic, anti-inflammatory and/or control of intraocular pressure effects (if an IOP reducing agent is used), while maintaining mydriasis (if a mydriatic agent is used). To maximize the preemptive anti-inflammatory, analgesic (for certain applications), IOP reduction (for certain applications) and mydriatic (for certain applications) effects, the solutions of the present invention are most preferably applied pre-, intra- and postoperatively. By occupying the targeted receptors or inactivating or activating targeted enzymes prior to the initiation of significant operative trauma locally, the agents of the present solution modulate specific pathways to preemptively inhibit the targeted pathologic processes. If inflammatory mediators and processes are preemptively inhibited in accordance with the present invention before they can exert tissue damage, and the mediators of increases in intraocular pressure are likewise preemptively inhibited, the benefit is more substantial than if given after these processes have been initiated.

The irrigation solutions of the present invention include combinations of drugs, each solution acting on multiple receptors or enzymes. The drug agents are thus simultaneously effective against a combination of pathologic processes, including pain and inflammation, and/or processes mediating increases in intraocular pressure. The action of these agents is expected to be synergistic, in that the multiple receptor antagonists and inhibitory agonists of the present invention provide a disproportionately increased efficacy in combination relative to the efficacy of the individual agents.

Used perioperatively, the solution should result in a clinically significant decrease in operative site pain and inflammation relative to currently used irrigation fluids, thereby decreasing the patient's postoperative analgesic requirement and, where appropriate, allowing earlier patient recovery. It is also expected that preemptively controlling intraocular pressure should decrease the need to treat elevated intraocular procedure postoperatively.

V. DETAILED DESCRIPTION OF THE PREFERRED EMBODIMENT

The present invention provides irrigation solutions for perioperative local application to ocular tissues, including intraocular and topical application, which include multiple agents that act to inhibit inflammation, inhibit pain, effect mydriasis (dilation of the pupil), and/or to decrease or control intraocular pressure, wherein the multiple agents are selected to act on multiple, differing molecular targets to achieve multiple differing physiologic functions. The irrigation solutions of the present invention are dilute solutions of multiple pain/inflammation inhibitory agents, IOP reducing agents, and/or mydriatic agents in a physiologic liquid irrigation carrier. The carrier is suitably an aqueous solution that may include physiologic electrolytes, such as normal saline or lactated Ringer's solution. More preferably, the carrier includes sufficient electrolytes to provide a physiological balanced salt solution, a cellular energy source, a buffering agent and a free-radical scavenger.

A solution in accordance with the present invention can include (a) one or more anti-inflammatory agents in combination with one or more analgesic agents, and optionally may also include one or more agents that act to reduce intraocular pressure ("IOP reducing agents") and/or mydriatic agents; (b) one or more anti-inflammatory agents in combination with one or more IOP reducing agents, and optionally one or more analgesic and/or mydriatic agents; (c) one or more anti-inflammatory agents in combination with one or more mydriatic agents, and optionally one or more analgesic agents and/or IOP reducing agents; (d) one or more analgesic agents in combination with one or more IOP reducing agents, and optionally one or more anti-inflammatory agents and/or mydriatic agents; (e) one or more analgesic agents in combination with one or more mydriatic agents, and optionally one or more anti-inflammatory agents and/or IOP reducing agents; or (f) one or more mydriatic agents in combination with one or more IOP reducing agents, and optionally one or more anti-inflammatory and/or analgesic agents.

Any of these solutions of the present invention may also include one or more antibiotic agents. Suitable antibiotics for use in the present invention include ciprofloxacin, gentamicin, tobramycin and ofloxacin. Other antibiotics that are suitable for perioperative intraocular use are also encompassed by the present invention. Suitable concentrations for one antibiotic suitably included in the irrigation solutions of the present invention, ciprofloxacin, are 0.01 millimolar to 10 millimolar, preferably 0.05 millimolar to 3 millimolar, most preferably 0.1 millimolar to 1 millimolar. Different antibiotics will be applied at different concentrations, as may be readily determined.

In each of the surgical solutions of the present invention, the agents are included in low concentrations and are delivered locally in low doses relative to concentrations and doses required with conventional methods of drug administration to achieve the desired therapeutic effect. It is impossible to obtain an equivalent therapeutic effect by delivering similarly dosed agents via systemic (e.g., intravenous, subcutaneous, intramuscular or oral) routes of drug administration since drugs given systemically are subject to first- and second-pass metabolism.

The concentration of each agent may be determined in part based on its dissociation constant, $K_d$. As used herein, the term "dissociation constant" is intended to encompass both the equilibrium dissociation constant for its respective agonist-receptor or antagonist-receptor interaction and the equilibrium inhibitory constant for its respective activator-enzyme or inhibitor-enzyme interaction. Each agent is preferably included at a low concentration of 0.1 to 10,000 times $K_d$, except for cyclooxygenase inhibitors, which may be required at larger concentrations depending on the particular inhibitor selected. Preferably, each agent is included at a concentration of 1.0 to 1,000 times $K_d$ and most preferably at approximately 100 times $K_d$. These concentrations are adjusted as needed to account for dilution in the absence of metabolic transformation at the local delivery site. The exact agents selected for use in the solution, and the concentration of the agents, varies in accordance with the particular application.

The surgical solutions constitute a novel therapeutic approach by combining multiple pharmacologic agents acting at distinct receptor and enzyme molecular targets. To date, pharmacologic strategies have focused on the development of highly specific drugs that are selective for individual receptor subtypes and enzyme isoforms that mediate responses to individual signaling neurotransmitters and hormones. This standard pharmacologic strategy, although well accepted, is not optimal since many other agents simultaneously may be responsible for initiating and maintaining a physiologic effect. Furthermore, despite inactivation of a single receptor subtype or enzyme, activation of other receptor subtypes or enzymes and the resultant signal transmission often can trigger a cascade effect. This explains the significant difficulty in employing a single receptor-specific drug to block a pathophysiologic process in which multiple transmitters play a role. Therefore, targeting only a specific individual receptor subtype is likely to be ineffective.

In contrast to the standard approach to pharmacologic therapy, the therapeutic approach of the present surgical solutions is based on the rationale that a combination of drugs acting simultaneously on distinct molecular targets is required to inhibit the full spectrum of events that underlie the development of a pathophysiologic state. Furthermore, instead of targeting a specific receptor subtype alone, the surgical solutions are composed of drugs that target common molecular mechanisms operating in different cellular physiologic processes involved in the development of pain and inflammation, the reduction in intraocular pressure, and the promotion of mydriasis. In this way, the cascading of additional receptors and enzymes in the nociceptive, inflammatory, and intraocular-pressure-increasing pathways is minimized by the surgical solutions. In these pathophysiologic pathways, the surgical solutions can inhibit the cascade effect both "upstream" and "downstream" (i.e., both at points of divergence and convergence of pathophysiologic pathways).

Preferred solutions of the present invention for use during ophthalmologic surgical procedures include one or more anti-inflammatory agents in combination with one or more mydriatic agents. Such preferred solutions may also include one or more analgesic agents and/or one or more IOP reducing agents, depending on whether a given procedure or condition treated thereby is associated with a high incidence of pain or increased intraocular procedure, respectively.

These agents are included at dilute concentrations in a physiologic aqueous carrier, such as any of the above-described carriers, e.g., a balanced salt solution. The solution may also include a viscosity increasing agent, e.g., a biocompatible and biodegradable polymer, for longer intraocular retention. The concentrations of the agents are determined in accordance with the teachings of the invention for direct, local application to ocular tissues during a surgical procedure. Application of the solution is carried out perioperatively, i.e.: intra-operatively; pre- and intra-operatively; intra- and post-operatively; or pre-, intra- and post-operatively. The agents may be provided in a stable one-part or two-part solution, or may be provided in a lyophilized form to which a one-part or two-part carrier liquid is added prior to use.

Functional classes of ophthalmologic agents that would be advantageous for use in perioperative ophthalmologic irrigation solutions of the present invention are now further described.

A. Anti-Inflammatory Agents

Preferred anti-inflammatory agents for use in the ophthalmologic solutions of the present invention include topical steroids, topical non-steroidal anti-inflammatory drugs (NSAIDs) and specific classes of anti-inflammatory agents that are suitably used intraocularly, such as topical anti-histamines, mast cell inhibitors and inhibitors of inducible nitric oxide synthase (iNOS). Other anti-inflammatory agents described below as pain/inflammation inhibitory agents, and other anti-inflammatory agents not disclosed herein, which are suitable for ocular use, are also intended to be encompassed by the present invention.

Examples of steroids that are believed to be suitable for use in the present invention include dexamethasone, fluorometholone and prednisolone. Examples of NSAIDS that are believed to be suitable include flurbiprofen, suprofen, diclofenac, ketoprofen and ketorolac. Selection of an NSAID will depend in part on a determination that excessive bleeding will not result. Examples of anti-histamines that are believed to be suitable include levocabastine, emedastine and olopatadine. Examples of mast cell inhibitors that are believed to be suitable include cromolyn sodium, lodoxamide and nedocromil. Examples of agents that act as both anti-histamine agents and mast cell inhibitors, and which are suitable for use in the present invention, include ketotifen and azelastine Inhibitors of iNOS that are believed to be suitable include $N^G$-monomethyl-L-arginine, 1400 W, diphenyleneiodium, S-methyl isothiourea, S-(aminoethyl) isothiourea, L-$N^6$-(1-iminoethyl)lysine, 1,3-PBITU, and 2-ethyl-2-thiopseudourea.

B. Analgesic Agents

The term "analgesic agent" as used herein with reference to ophthalmologic solutions and methods is intended to encompass both agents that provide analgesia and agents that provide local anesthesia. Preferred analgesic agents for use in the ophthalmologic solutions of the present invention include topical local anesthetics and topical opioids. Other analgesic agents described below as pain/inflammation inhibitory agents, and other analgesic agents not disclosed herein, which are suitable for ocular use, are also intended to be encompassed by the present invention.

Examples of local anesthetics that are believed to be suitable for use in the present invention include lidocaine, tetracaine, bupivacaine and proparacaine. Examples of opioids that are believed to be suitable for use in the present invention include morphine, fentanyl and hydromorphone.

C. Mydriatic Agents

Preferred mydriatic agents for use in the ophthalmologic solutions of the present invention, to dilate the pupil during surgery, include sympathomimetics, including alpha-1 adrenergic receptor agonists, and anticholinergic agents, including anti-muscarinics. Anticholinergic agents may be selected when longer action is desired, because they provide both cycloplegia (paralysis of the ciliary muscle) and mydriasis, e.g., tropicamide exhibits a half-life of approximately 4-6 hours. However, for many procedures, alpha-1 adrenergics will be preferred because they provide mydriasis but not cycloplegia. Alpha-1 adrenergics are thus shorter acting, causing mydriasis during a surgical procedure and allowing the pupil to return to its normal state shortly after completion of the procedure. Examples of suitable adrenergic receptor agonists active at alpha-1 receptors include phenylephrine, epinephrine and oxymetazoline. Examples of suitable anticholinergic agents include tropicamide, cyclopentolate, atropine and homatropine. Other agents that cause mydriasis, and particularly short-acting mydriatic agents, are also intended to be encompassed by the present invention.

D. Agents that Decrease Intraocular Pressure

Preferred agents that decrease intraocular pressure for use in the ophthalmologic solutions of the present invention include beta adrenergic receptor antagonists, carbonic anhydrase inhibitors, alpha-2 adrenergic receptor agonists and prostaglandin agonists. Examples of suitable beta adrenergic receptor antagonists are believed to include timolol, metipranolol and levobunolol. Examples of suitable carbonic anhydrase inhibitors are believed to include brinzolamide and dorzolamide. Examples of suitable alpha-2 adrenergic receptor agonists are believed to include apraclonidine, brimonidine and oxymetazoline. Other alpha-2 adrenergic receptor agonists suitable for ocular use and described below as inflammatory/pain inhibitory agents may also suitably function as IOP reducing agents within the solutions of the present invention. Suitable prostaglandin agonists are believed to include latanoprost, travoprost and bimatoprost. When inflammation inhibition is a primary desired effect of the solution, and IOP control is needed, an IOP reducing agent other than a prostaglandin agonist may suitably be selected; to avoid the possibility that prostaglandin may enhance post-surgical inflammation. Other agents that decrease intraocular pressure are also intended to be encompassed by the present invention.

E. Pain/Inflammation Inhibitory Agents

The following agents, referred to herein as pain/inflammation inhibitory agents, may be suitable for use in the ophthalmologic solutions and methods of the present invention as analgesic and/or anti-inflammatory agents. The particular class(es) of agent, and individual agent(s) within a class, to be utilized for a particular ophthalmologic application can be readily determined by those of skill in the art in accordance with the present invention.

For example, ocular inflammation models in the rabbit have been studied by comparison of the inflammation response induced by the topical application of several irritating agents, specifically carrageenan, Freund's adjuvant, alkali and croton oil. The methods involve measurement of the following parameters which can be determined after the application of each irritant to the eyes of female, white, New Zealand rabbits: corneal edema and the Tyndall effect (slit-lamp biomicroscopy), corneal thickness (biometer-pachometer) and aqueous humor levels of the prostaglandin E2 (R.I.A), total protein (Weichselbaum technique), albumin, albumin/globulin (Doumas technique) and leukocytes (coulter counter).

Validation studies have found that Croton oil 1-4% (40 µl) produced edema and a Tyndall effect that showed a proportional increase with croton oil concentration. Ultrasonic pachometer measurement of the variation in corneal thickness (3-168 h) showed a dose-dependent response ($p<0.01$) from the 8th to the 168th hour. Uveitis and considerable increases in the levels of the prostaglandin E2 ($4.50\pm0.40$ pg/0.1 ml vs. $260.03\pm2.03$ pg/0.1 ml), total protein ($0.25\pm0.05$ g/l vs. $2.10\pm0.08$ g/l), albumin, albumin/globulin and leukocytes were observed in the aqueous humor 24 hours after topical application of croton oil 3% (40 µl). All the values obtained were statistically significant ($p<0.01$).

The topical application of 3% croton oil (40 µl) is most appropriate for the evaluation of the inflammatory process in the anterior chamber and for the determination of the effects of intraocular penetration. The inflammatory mechanism in this model is thought to involve the activation of the arachidonic acid pathway accompanied by the breakdown of the blood-aqueous barrier permitting high molecular weight proteins to enter the aqueous humor.

The above models can be used to test the efficacy of drugs applied topically, such as by irrigation, in inhibiting inflammatory processes and effecting other ocular functions. A given agent or combination of agents to be evaluated is applied to the eyes of rabbits after the application of each irritant to the eyes.

The solution may suitably include agents selected from the following classes of receptor antagonists and agonists and enzyme activators and inhibitors, each class acting through a differing molecular mechanism of action for pain and inflammation inhibition: (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin$_1$ and neurokinin$_2$ receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA$_2$ isoform inhibitors and PLC$_\gamma$ isoform inhibitors, (b) cyclooxygenase inhibitors, and (c) lipoxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene B$_4$ receptor subtype antagonists and leukotriene D$_4$ receptor subtype antagonists; (12) opioid receptor agonists, including μ-opioid, δ-opioid, and κ-opioid receptor subtype agonists; (13) purinoceptor agonists and antagonists including P$_{2X}$ receptor antagonists and P$_{2Y}$ receptor agonists; (14) adenosine triphosphate (ATP)-sensitive potassium channel openers; (15) local anesthetics; and (16) alpha-2 adrenergic receptor agonists. Each of the above agents functions either as an anti-inflammatory agent and/or as an analgesic, i.e., anti-pain, agent. The selection of agents from these classes of compounds is tailored for the particular application.

1. Serotonin Receptor Antagonists

Serotonin (5-HT) is thought to produce pain by stimulating serotonin$_2$ (5-HT$_2$) and/or serotonin$_3$ (5-HT$_3$) receptors on nociceptive neurons in the periphery. Most researchers agree that 5-HT$_3$ receptors on peripheral nociceptors mediate the immediate pain sensation produced by 5-HT. In addition to inhibiting 5-HT-induced pain, 5-HT$_3$ receptor antagonists, by inhibiting nociceptor activation, also may inhibit neurogenic inflammation. Activation of 5-HT$_2$ receptors also may play a role in peripheral pain and neurogenic inflammation. One goal of the solution of the present invention is to block pain and a multitude of inflammatory processes. Thus, 5-HT$_2$ and 5-HT$_3$ receptor antagonists may both be suitably used, either individually or together, in the solution of the present invention. Amitriptyline (Elavil™) is believed to be a potentially suitable 5-HT$_2$ receptor antagonist for use in the present invention. Metoclopramide (Reglan™) is used clinically as an anti-emetic drug, but displays moderate affinity for the 5-HT$_3$ receptor and can inhibit the actions of 5-HT at this receptor, possibly inhibiting the pain due to 5-HT release from platelets. Thus, it may also be suitable for use in the present invention.

Other potentially suitable 5-HT$_2$ receptor antagonists include imipramine, trazodone, desipramine, ketanserin. Other suitable 5-HT$_3$ antagonists include cisapride and ondansetron. Therapeutic and preferred concentrations for use of these drugs in the solution of the present invention are set forth in Table 1.

TABLE 1

Therapeutic and Preferred Concentrations of Pain/Inflammation Inhibitory Agents

| Class of Agent | Therapeutic Concentrations (Nanomolar) | Preferred Concentrations (Nanomolar) |
| --- | --- | --- |
| Serotonin$_2$ Receptor Antagonists: | | |
| amitriptyline | 0.1-1,000 | 50-500 |
| imipramine | 0.1-1,000 | 50-500 |
| trazodone | 0.1-2,000 | 50-500 |
| desipramine | 0.1-1,000 | 50-500 |
| ketanserin | 0.1-1,000 | 50-500 |
| Serotonin$_3$ Receptor Antagonists: | | |
| tropisetron | 0.01-100 | 0.05-50 |
| metoclopramide | 10-10,000 | 200-2,000 |
| cisapride | 0.1-1,000 | 20-200 |
| ondansetron | 0.1-1,000 | 20-200 |

2. Serotonin Receptor Agonists

5-HT$_{1A}$, 5-HT$_{1B}$ and 5-HT$_{1D}$ receptors are known to inhibit adenylate cyclase activity. Thus including a low dose of these serotonin$_{1A}$, serotonin$_{1B}$ and serotonin$_{1D}$ receptor agonists in the solution should inhibit neurons mediating pain and inflammation. The same action is expected from serotonin$_{1E}$ and serotonin$_{1F}$ receptor agonists because these receptors also inhibit adenylate cyclase.

Buspirone is a potentially suitable 1A receptor agonist for use in the present invention. Sumatriptan is a potentially suitable 1A, 1B, 1D and 1F receptor agonist. A potentially suitable 1B and 1D receptor agonist is dihydroergotamine. A suitable 1E receptor agonist is ergonovine. Therapeutic and preferred concentrations for these receptor agonists are provided in Table 2.

TABLE 2

Therapeutic and Preferred Concentrations of Pain/Inflammation Inhibitory Agents

| Class of Agent | Therapeutic Concentrations (Nanomolar) | Preferred Concentrations (Nanomolar) |
| --- | --- | --- |
| Serotonin$_{1A}$ Agonists: | | |
| 5-carboxyamidotryptamine | 1-1,000 | 10-200 |
| sumatriptan | 1-1,000 | 10-200 |
| Serotonin$_{1B}$ Agonists: | | |
| CP93129 | 0.1-1,000 | 10-100 |
| sumatriptan | 1-1,000 | 10-200 |
| Serotonin$_{1D}$ Agonists: | | |
| naratriptan | 0.1-1,000 | 10-100 |
| sumatriptan | 1-1,000 | 10-200 |
| Serotonin$_{1E}$ Agonists: | | |
| ergonovine | 10-2,000 | 100-1,000 |
| Serotonin$_{1F}$ Agonists: | | |
| sumatriptan | 1-1,000 | 10-200 |

3. Histamine Receptor Antagonists

Histamine receptor antagonists may potentially be included in the irrigation solution. Promethazine (Phenergan™) is a commonly used anti-emetic drug that potently blocks $H_1$ receptors, and is potentially suitable for use in the present invention. Other potentially suitable $H_1$ receptor antagonists include terfenadine, diphenhydramine, amitriptyline, mepyramine and tripolidine. Because amitriptyline is also effective as a serotonin$_2$ receptor antagonist, it has a dual function as used in the present invention. Suitable therapeutic and preferred concentrations for each of these $H_1$ receptor antagonists are set forth in Table 3.

TABLE 3

Therapeutic and Preferred Concentrations of Pain/Inflammation Inhibitory Agents

| Class of Agent Histamine$_1$ Receptor Antagonists: | Therapeutic Concentrations (Nanomolar) | Preferred Concentrations (Nanomolar) |
|---|---|---|
| promethazine | 0.1-1,000 | 50-200 |
| diphenhydramine | 0.1-1,000 | 50-200 |
| amitriptyline | 0.1-1,000 | 50-500 |
| terfenadine | 0.1-1,000 | 50-500 |
| mepyramine (pyrilamine) | 0.1-1,000 | 5-200 |
| tripolidine | 0.01-100 | 5-20 |

4. Bradykinin Receptor Antagonists

Bradykinin receptors generally are divided into bradykinin$_1$ (B$_1$) and bradykinin$_2$ (B$_2$) subtypes. These drugs are peptides (small proteins), and thus they cannot be taken orally, because they would be digested. Antagonists to B$_2$ receptors block bradykinin-induced acute pain and inflammation. B$_1$ receptor antagonists inhibit pain in chronic inflammatory conditions. Depending on the application, the solution of the present invention may suitably include either or both bradykinin B$_1$ and B$_2$ receptor antagonists. Potentially suitable bradykinin$_1$ receptor antagonists for use in the present invention include: the [des-Arg$^{10}$] derivative of D-Arg-(Hyp$^3$-Thi$^5$-D-Tic$^7$-Oic$^8$)-BK ("the [des-Arg$^{10}$] derivative of HOE 140", available from Hoechst Pharmaceuticals); and [Leu$^8$] des-Arg$^9$-BK. Potentially suitable bradykinin$_2$ receptor antagonists include: [D-Phe$^7$]-BK; D-Arg-(Hyp$^3$-Thi$^{5,8}$-D-Phe$^7$)-BK ("NPC 349"); D-Arg-(Hyp$^3$-D-Phe$^7$)-BK ("NPC 567"); and D-Arg-(Hyp$^3$-Thi$^5$-D-Tic$^7$-Oic$^8$)-BK ("HOE 140"). Suitable therapeutic and preferred concentrations are provided in Table 4.

TABLE 4

Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| Bradykinin$_1$ Receptor Antagonists: | | |
| [Leu$^8$] des-Arg$^9$-BK | 1-1,000 | 50-500 |
| [des-Arg$^{10}$] derivative of HOE 140 | 1-1,000 | 50-500 |
| [leu$^9$] [des-Arg$^{10}$] kalliden | 0.1-500 | 10-200 |
| Bradykinin$_2$ Receptor Antagonists: | | |
| [D-Phe$^7$]-BK | 100-10,000 | 200-5,000 |
| NPC 349 | 1-1,000 | 50-500 |
| NPC 567 | 1-1,000 | 50-500 |
| HOE 140 | 1-1,000 | 50-500 |

5. Kallikrein Inhibitors

The peptide bradykinin is an important mediator of pain and inflammation. Bradykinin is produced as a cleavage product by the action of kallikrein on high molecular weight kininogens in plasma. Therefore, kallikrein inhibitors are believed to be therapeutic in inhibiting bradykinin production and resultant pain and inflammation. A potentially suitable kallikrein inhibitor for use in the present invention is aprotinin. Potentially suitable concentrations for use in the solutions of the present invention are set forth below in Table 5.

TABLE 5

Therapeutic and Preferred Concentrations of Pain/Inflammation Inhibitory Agents

| Class of Agent Kallikrein Inhibitor: | Therapeutic Concentrations (Nanomolar) | Preferred Concentrations (Nanomolar) |
|---|---|---|
| aprotinin | 0.1-1,000 | 50-500 |

6. Tachykinin Receptor Antagonists

Tachykinins (TKs) are a family of structurally related peptides that include substance P, neurokinin A (NKA) and neurokinin B (NKB). Neurons are the major source of TKs in the periphery. An important general effect of TKs is neuronal stimulation, but other effects include endothelium-dependent vasodilation, plasma protein extravasation, mast cell recruitment and degranulation and stimulation of inflammatory cells. Due to the above combination of physiological actions mediated by activation of TK receptors, targeting of TK receptors is a reasonable approach for the promotion of analgesia and the treatment of neurogenic inflammation.

a. Neurokinin$_1$ Receptor Subtype Antagonists

Substance P activates the neurokinin receptor subtype referred to as NK$_1$. A potentially suitable Substance P antagonist is ([D-Pro$^9$-[spiro-gamma-lactam]Leu$^{10}$,Trp$^{11}$]physalaemin-(1-11)) ("GR 82334"). Other potentially suitable antagonists for use in the present invention which act on the NK$_1$ receptor are: 1-imino-2-(2-methoxy-phenyl)-ethyl)-7,7-diphenyl-4-perhydroisoindolone(3 aR,7aR) ("RP 67580"); and 2S,3S-cis-3-(2-methoxybenzylamino)-2-benzhydrylquinuclidine ("CP 96,345"). Suitable concentrations for these agents are set forth in Table 6.

TABLE 6

Therapeutic and Preferred Concentrations of Pain/Inflammation Inhibitory Agents

| Class of Agent Neurokinin$_1$ Receptor Subtype Antagonists | Therapeutic Concentrations (Nanomolar) | Preferred Concentrations (Nanomolar) |
|---|---|---|
| GR 82334 | 1-1,000 | 10-500 |
| CP 96,345 | 1-10,000 | 100-1,000 |
| RP 67580 | 0.1-1,000 | 100-1,000 | b. Neurokinin$_2$ Receptor Subtype Antagonists

Neurokinin A is a peptide which is colocalized in sensory neurons with substance P and which also promotes inflammation and pain. Neurokinin A activates the specific neurokinin receptor referred to as NK$_2$. Examples of potentially suitable NK$_2$ antagonists include: ((S)—N-methyl-N-[4-(4-acetylamino-4-phenylpiperidino)-2-(3,4-dichlorophenyl)butyl]benzamide ("(±)-SR 48968"); Met-Asp-Trp-Phe-Dap- Leu ("MEN 10,627"); and cyc(Gln-Trp-Phe-Gly-Leu-Met) ("L 659,877"). Suitable concentrations of these agents are provided in Table 7.

TABLE 7

Therapeutic and Preferred Concentrations of Pain/Inflammation Inhibitory Agents

| Class of Agent Neurokinin$_2$ Receptor Subtype Antagonists: | Therapeutic Concentrations (Nanomolar) | Preferred Concentrations (Nanomolar) |
|---|---|---|
| MEN 10,627 | 1-1,000 | 10-1,000 |
| L 659,877 | 10-10,000 | 100-10,000 |
| (±)-SR 48968 | 10-10,000 | 100-10,000 |

7. CGRP Receptor Antagonists

Calcitonin gene-related peptide (CGRP) is a peptide which is also colocalized in sensory neurons with substance P, and which acts as a vasodilator and potentiates the actions of substance P. An example of a potentially suitable CGRP receptor antagonist is I-CGRP-(8-37), a truncated version of CGRP. This polypeptide inhibits the activation of CGRP receptors. Suitable concentrations for this agent are provided in Table 8.

TABLE 8

Therapeutic and Preferred Concentrations of Pain/Inflammation Inhibitory Agents

| Class of Agent CGRP Receptor Antagonist: | Therapeutic Concentrations (Nanomolar) | Preferred Concentrations (Nanomolar) |
|---|---|---|
| I-CGRP-(8-37) | 1-1,000 | 10-500 |

8. Interleukin Receptor Antagonist

Interleukins are a family of peptides, classified as cytokines, produced by leukocytes and other cells in response to inflammatory mediators. Interleukins (IL) may be potent hyperalgesic agents peripherally. An example of a potentially suitable IL-1β receptor antagonist is Lys-D-Pro-Thr, which is a truncated version of IL-1β. This tripeptide inhibits the activation of IL-1β receptors. Suitable concentrations for this agent are provided in Table 9.

TABLE 9

Therapeutic and Preferred Concentrations of Pain/Inflammation Inhibitory Agents

| Class of Agent Interleukin Receptor Antagonist: | Therapeutic Concentrations (Nanomolar) | Preferred Concentrations (Nanomolar) |
|---|---|---|
| Lys-D-Pro-Thr | 1-1,000 | 10-500 |

9 Inhibitors of Enzymes Active in the Synthetic Pathway for Arachidonic Acid Metabolites a. Phospholipase Inhibitors

The production of arachidonic acid by phospholipase A$_2$ (PLA$_2$) results in a cascade of reactions that produces numerous mediators of inflammation, known as eicosanoids. There are a number of stages throughout this pathway that can be inhibited, thereby decreasing the production of these inflammatory mediators. Examples of inhibition at these various stages are given below.

Inhibition of the enzyme PLA$_2$ isoform inhibits the release of arachidonic acid from cell membranes, and therefore inhibits the production of prostaglandins and leukotrienes resulting in decreased inflammation and pain. An example of a potentially suitable PLA$_2$ isoform inhibitor is manoalide. Suitable concentrations for this agent are included in Table 10. Inhibition of the phospholipase C (PLC) isoform also will result in decreased production of prostanoids and leukotrienes and, therefore, will result in decreased pain and inflammation. An example of a PLC isoform inhibitor is 1-[6-((17β-3-methoxyestra-1,3,5 (10)-trien-17-yl)amino)hexyl]-1H-pyrrole-2,5-dione.

TABLE 10

Therapeutic and Preferred Concentrations of Pain/Inflammation Inhibitory Agents

| Class of Agent PLA$_2$ Isoform Inhibitor: | Therapeutic Concentrations (Nanomolar) | Preferred Concentrations (Nanomolar) |
|---|---|---|
| manoalide | 100-100,000 | 500-10,000 | b. Cyclooxygenase Inhibitors

Nonsteroidal anti-inflammatory drugs (NSAIDs) are widely used as anti-inflammatory and analgesic agents. The molecular targets for these drugs are type I and type II cyclooxygenases (COX-1 and COX-2). Constitutive activity of COX-1 and induced activity of COX-2 both lead to synthesis of prostaglandins that contribute to pain and inflammation.

NSAIDs currently on the market (diclofenac, naproxen, indomethacin, ibuprofen, etc.) are generally nonselective inhibitors of both isoforms of COX, but may show greater selectively for COX-1 over COX-2, although this ratio varies for the different compounds. Use of COX-1 and COX-2 inhibitors to block formation of prostaglandins represents a better therapeutic strategy than attempting to block interactions of the natural ligands with the seven described subtypes of prostanoid receptors.

Potentially suitable cyclooxygenase inhibitors for use in the present invention are ketoprofen, ketorolac and indomethacin. Therapeutic and preferred concentrations of these agents for use in the solution are provided in Table 11. For some applications, it may also be suitable to utilize a COX-2 specific inhibitor (i.e., selective for COX-2 relative to COX-1) as an anti-inflammatory/analgesic agent. Potentially suitable COX-2 inhibitors include rofecoxib (MK 966), SC-58451, celecoxib (SC-58125), meloxicam, nimesulide, diclofenac, NS-398, L-745,337, RS57067, SC-57666 and flosulide.

TABLE 11

Therapeutic and Preferred Concentrations of
Pain/Inflammation Inhibitory Agents

| Class of Agent<br>Cyclooxygenase Inhibitors: | Therapeutic<br>Concentrations<br>(Nanomolar) | Preferred<br>Concentrations<br>(Nanomolar) |
|---|---|---|
| ketorolac | 100-10,000 | 500-5,000 |
| ketoprofen | 100-10,000 | 500-5,000 |
| indomethacin | 1,000-500,000 | 10,000-200,000 | c. Lipooxygenase Inhibitors

Inhibition of the enzyme lipooxygenase inhibits the production of leukotrienes, such as leukotriene $B_4$, which is known to be an important mediator of inflammation and pain. An example of a potentially suitable 5-lipooxygenase antagonist is 2,3,5-trimethyl-6-(12-hydroxy-5,10-dodecadiynyl)-1,4-benzoquinone ("AA 861"), suitable concentrations for which are listed in Table 12.

TABLE 12

Therapeutic and Preferred Concentrations of
Pain/Inflammation Inhibitory Agents

| Class of Agent<br>Lipooxygenase Inhibitor: | Therapeutic<br>Concentrations<br>(Nanomolar) | Preferred<br>Concentrations<br>(Nanomolar) |
|---|---|---|
| AA 861 | 100-10,000 | 500-5,000 |

10. Prostanoid Receptor Antagonists

Specific prostanoids produced as metabolites of arachidonic acid mediate their inflammatory effects through activation of prostanoid receptors. Examples of classes of specific prostanoid antagonists are the eicosanoid EP-1 and EP-4 receptor subtype antagonists and the thromboxane receptor subtype antagonists. A potentially suitable prostaglandin $E_2$ receptor antagonist is 8-chlorodibenz[b,f][1,4]oxazepine-10 (11H)-carboxylic acid, 2-acetylhydrazide ("SC 19220"). A potentially suitable thromboxane receptor subtype antagonist is [15-[1α,2β(5Z),3β,4α]-7-[3-[2-(phenylamino)-carbonyl]hydrazino]methyl]-7-oxobicyclo-[2,2,1]-hept-2-yl]-5-heptanoic acid ("SQ 29548"). Suitable concentrations for these agents are set forth in Table 13.

TABLE 13

Therapeutic and Preferred Concentrations of
Pain/Inflammation Inhibitory Agents

| Class of Agent<br>Eicosanoid EP-1 Antagonist: | Therapeutic<br>Concentrations<br>(Nanomolar) | Preferred<br>Concentrations<br>(Nanomolar) |
|---|---|---|
| SC 19220 | 100-10,000 | 500-5,000 |

11. Leukotriene Receptor Antagonists

The leukotrienes ($LTB_4$, $LTC_4$, and $LTD_4$) are products of the 5-lipooxygenase pathway of arachidonic acid metabolism that are generated enzymatically and have important biological properties. Leukotrienes are implicated in a number of pathological conditions including inflammation. An example of a potentially suitable leukotriene $B_4$ receptor antagonist is SC (+)-(S)-7-(3-(2-(cyclopropylmethyl)-3-methoxy-4-[(methylamino)-carbonyl]phenoxy(propoxy)-3,4-dihydro-8-propyl-2H-1-benzopyran-2-propanoicacid ("SC 53228"). Concentrations for this agent that are potentially suitable for the practice of the present invention are provided in Table 14. Other potentially suitable leukotriene $B_4$ receptor antagonists include [3-[-2(7-chloro-2-quinolinyl)ethenyl]phenyl][[3-(dimethylamino-3-oxopropyl)thio]methyl]thiopropanoic acid ("MK 0571") and the drugs LY 66,071 and ICI 20,3219. MK 0571 also acts as a $LTD_4$ receptor subtype antagonist.

TABLE 14

Therapeutic and Preferred Concentrations of
Pain/Inflammation Inhibitory Agents

| Class of Agent<br>Leukotriene $B_4$ Antagonist: | Therapeutic<br>Concentrations<br>(Nanomolar) | Preferred<br>Concentrations<br>(Nanomolar) |
|---|---|---|
| SC 53228 | 100-10,000 | 500-5,000 |

12. Opioid Receptor Agonists

Activation of opioid receptors results in anti-nociceptive effects and, therefore, agonists to these receptors are desirable. Opioid receptors include the μ-, δ- and κ-opioid receptor subtypes. Examples of potentially suitable μ-opioid receptor agonists are fentanyl and Try-D-Ala-Gly-[N-MePhe]-NH ($CH_2$)—OH ("DAMGO"). An example of a potentially suitable δ-opioid receptor agonist is [D-Pen$^2$,D-Pen$^5$]enkephalin ("DPDPE"). An example of a potentially suitable κ-opioid receptor agonist is (trans)-3,4-dichloro-N-methyl-N-[2-(1-pyrrolidnyl)cyclohexyl]-benzene acetamide ("U50,488"). Suitable concentrations for each of these agents are set forth in Table 15.

TABLE 15

Therapeutic and Preferred Concentrations of
Pain/Inflammation Inhibitory Agents

| Class of Agent | Therapeutic<br>Concentrations<br>(Nanomolar) | Preferred<br>Concentrations<br>(Nanomolar) |
|---|---|---|
| μ-Opioid Agonist: | | |
| DAMGO | 0.1-100 | 0.5-20 |
| sufentanyl | 0.01-50 | 1-20 |
| fentanyl | 0.1-500 | 10-200 |
| PL 017 | 0.05-50 | 0.25-10 |
| δ-Opioid Agonist: | | |
| DPDPE | 0.1-500 | 1.0-100 |
| κ-Opioid Agonist: | | |
| U50,488 | 0.1-500 | 1.0-100 |

13. Purinoceptor Antagonists and Agonists

Extracellular ATP acts as a signaling molecule through interactions with $P_2$ purinoceptors. One major class of purinoceptors are the $P_{2X}$ purinoceptors which are ligand-gated ion channels possessing intrinsic ion channels permeable to $Na^+$, $K^+$, and $Ca^{2+}$. Potentially suitable antagonists of $P_{2X}$/ATP purinoceptors for use in the present invention include, by way of example, suramin and pyridoxylphosphate-6-azophenyl-2,4-disulfonic acid ("PPADS"). Suitable concentrations for these agents are provided in Table 16. Agonists of the $P_{2Y}$ receptor, a G-protein coupled receptor, are known to effect smooth muscle relaxation through elevation of inositol triphosphate ($IP_3$) levels with a subsequent increase in intracellular calcium. An example of a $P_{2Y}$ receptor agonist is 2-me-S-ATP.

TABLE 16

Therapeutic and Preferred Concentrations of Pain/Inflammation Inhibitory Agents

| Class of Agent Purinoceptor Antagonists: | Therapeutic Concentrations (Nanomolar) | Preferred Concentrations (Nanomolar) |
|---|---|---|
| suramin | 100-100,000 | 10,000-100,000 |
| PPADS | 100-100,000 | 10,000-100,000 |

14. Adenosine Triphosphate (ATP)-Sensitive Potassium Channel Openers

Potentially suitable ATP-sensitive $K^+$ channel openers for the practice of the present invention include: (−)pinacidil; cromakalim; nicorandil; minoxidil; N-cyano-N'-[1,1-dimethyl-[2,2,3,3-$^3$H]propyl]-N"-(3-pyridinyl)guanidine ("P 1075"); and N-cyano-N'-(2-nitroxyethyl)-3-pyridinecarboximidamide monomethansulphonate ("KRN 2391"). Concentrations for these agents are set forth in Table 17.

TABLE 17

Therapeutic and Preferred Concentrations of Pain/Inflammation Inhibitory Agents

| Class of Agent ATP-Sensitive $K^+$ Channel Opener: | Therapeutic Concentrations (Nanomolar) | Preferred Concentrations (Nanomolar) |
|---|---|---|
| cromakalim | 10-10,000 | 100-10,000 |
| nicorandil | 10-10,000 | 100-10,000 |
| minoxidil | 10-10,000 | 100-10,000 |
| P 1075 | 0.1-1,000 | 10-1,000 |
| KRN 2391 | 1-10,000 | 100-1,000 |
| (−)pinacidil | 1-10,000 | 100-1,000 |

15. Local Anesthetics

The solution of the present invention is preferably used for continuous infusion throughout the surgical procedure to provide preemptive inhibition of pain and inflammation. Local anesthetics (e.g., lidocaine, bupivacaine, etc.) are used clinically as analgesic agents and are known to reversibly bind to sodium channels in the membrane of neuronal axons, thereby inhibiting axonal conduction and the transmission of pain signals from the periphery to the spinal cord. The local delivery of extremely low or sub-clinical concentrations of lidocaine, a local anesthetic, has been shown to inhibit nerve injury discharge (Bisla K and Tanalian D L, Concentration-dependent Effects of Lidocaine on Corneal Epithelial Wound Healing, *Invest Ophthalmol Vis Sci* 33(11), pp. 3029-3033, 1992). Therefore, in addition to decreasing pain signals, local anesthetics, when delivered in extremely low concentrations, also have anti-inflammatory properties.

The inclusion of a local anesthetic in extremely low or "sub-anesthetic" concentrations in the irrigation solution provides a beneficial anti-inflammatory effect without exposing the patient to the systemic toxicity associated with currently used clinical doses of local anesthetics. Thus, in extremely low concentrations, a local anesthetic is suitable for use in the present invention. Examples of representative local anesthetics useful in the practice of the present invention include, without limitation, benzocaine, bupivacaine, chloroprocaine, cocaine, etiodocaine, lidocaine, mepivacaine, pramoxine, prilocaine, procaine, proparacaine, ropivacaine, tetracaine, dibucaine, QX-222, ZX-314, RAC-109, HS-37 and the pharmacologically active enantiomers thereof. Although not wishing to be bound by any particular theory, some local anesthetics are believed to act by inhibiting voltage-gated sodium channels. (See Guo, X. et al., "Comparative inhibition of voltage-gated cation channels by local anesthetics," *Ann. N.Y. Acad. Sci.* 625: 181-199 (1991)). Particularly useful pharmacologically active enantiomers of local anesthetics include, for example, the R-enantiomer of bupivacaine. For purposes of the present invention, useful concentrations of anesthetic agents delivered locally are generally in the range of about 125 to about 100,000,000 nanomolar, more preferably about 1,000 to about 10,000,000 nanomolar, and most preferably about 225,000 to about 1,000,000 nanomolar. In one embodiment, the solutions of the invention comprise at least one local anesthetic agent delivered locally at a concentration of no greater than 750,000 nanomolar. In other embodiments, the solutions of the invention comprise at least one local anesthetic agent delivered locally at a concentration of no greater than 500,000 nanomolar. Useful concentrations of representative specific local anesthetic agents are set forth below.

TABLE 18

Therapeutic and Preferred Concentrations of Specific Local Anesthetic Agents

| Local Anesthetics: | Concentrations (Nanomolar) | | |
|---|---|---|---|
| | Therapeutic | Preferred | More Preferred |
| lidocaine | 500-1,600,000 | 4,000-1,200,000 | 900,000-1,100,000 |
| bupivacaine | 125-400,000 | 1,000-300,000 | 225,000-275,000 |

16. Alpha-2 Adrenergic Receptor Agonists

All the individual nine receptors that comprise the adrenergic amine receptor family belong to the G-protein linked superfamily of receptors. The classification of the adrenergic family into three distinct subfamilies, namely $\alpha_1$ (alpha-1), $\alpha_2$ (alpha-2), and $\beta$ (beta), is based upon a wealth of binding, functional and second messenger studies. Each adrenergic receptor subfamily is itself composed of three homologous receptor subtypes that have been defined by cloning and pharmacological characterization of the recombinant receptors. Among adrenergic receptors in different subfamilies (alpha-1 vs. alpha-2 vs. beta), amino acid identities in the membrane spanning domain range from 36-73%. However, between members of the same subfamily ($\alpha_{1A}$ vs. $\alpha_{1B}$) the identity between membrane domains is usually 70-80%. Together, these distinct receptor subtypes mediate the effects of two physiological agonists, epinephrine and norepinephrine.

Distinct adrenergic receptor types couple to unique sets of G-proteins and are thereby capable of activating different signal transduction effectors. The classification of alpha-1, alpha-2, and beta subfamilies not only defines the receptors with regard to signal transduction mechanisms, but also accounts for their ability to differentially recognize various natural and synthetic adrenergic amines. In this regard, a number of selective ligands have been developed and utilized to characterize the pharmacological properties of each of these receptor types. Functional responses of alpha-1 receptors have been shown in certain systems to stimulate phosphatidylinositol turnover and promote the release of intracellular calcium (via $G_q$), while stimulation of alpha-2 receptors inhibits adenylyl cyclase (via $G_i$). In contrast, functional responses of beta receptors are coupled to increases in adenylyl cyclase activity and increases in intracellular calcium (via $G_s$).

It is now accepted that there are three different alpha-1 receptor subtypes which all exhibit a high affinity (subnanomolar) for the antagonist, prazosin. The subdivision of alpha-1 adrenoceptors into three different subtypes, designated $\alpha_{1A}$, $\alpha_{1B}$, and $\alpha_{1D}$, has been primarily based on extensive ligand binding studies of endogenous receptors and cloned receptors. Pharmacological characterization of the cloned receptors led to revisions of the original classification such that the clone originally called the $\alpha_{1C}$ subtype corresponds to the pharmacologically defined $\alpha_{1A}$ receptor. Agonist occupation of $\alpha_{1A-D}$ receptor subtypes results in activation of phospholipase C, stimulation of PI breakdown, generation of the $IP_3$ as second messenger and an increase in intracellular calcium.

Three different $\alpha_2$-receptor subtypes have been cloned, sequenced, and expressed in mammalian cells, referred to as $\alpha_{2A}$ ($\alpha_2$-C10), $\alpha_{2B}$ ($\alpha_2$-C2), $\alpha_{2C}$ ($\alpha_2$-C4). These subtypes not only differ in their amino acid composition but also in their pharmacological profiles and distributions. An additional $\alpha_2$-receptor subtype, $\alpha_{2D}$ (gene rg20), was originally proposed based on radioligand binding studies of rodent tissues but is now considered to represent a species homolog to the human $\alpha_{2A}$ receptor.

Functionally, the signal transduction pathways are similar for all three $\alpha_{2A}$ receptor subtypes; each is negatively coupled to adenylate cyclase via $G_{i/o}$. In addition, the $\alpha_{2A}$ and $\alpha_{2B}$ receptors have also been reported to mediate activation of a G-protein coupled potassium channel (receptor-operated) as well as inhibition of a G-protein associated calcium channel.

Pharmacologically, alpha-2 adrenergic receptors are defined as highly sensitive to the antagonists yohimbine (Ki=0.5-25 µM), atipamezole (Ki=0.5-2.5 µM), and idazoxan (Ki=21-35 µM) and with low sensitivity to the alpha-1 receptor antagonist prazosin. Agonists selective for the alpha-2 adrenergic receptor class relative to the alpha-1 adrenergic receptor class are UK14,304, BHT920 and BHT933. Oxymetazoline binds with high affinity and selectivity to the $\alpha_{2A}$-receptor subtype ($K_D$=3 µM), but in addition binds with high affinity to alpa-1 adrenergic receptors and 5HT1 receptors. An additional complicating factor is that alpha-2 adrenergic receptor ligands which are imidazolines (clonidine, idazoxan) and others (oxymetazoline and UK14304) also bind with high affinity (nanomolar) to non-adrenoceptor imidazoline binding sites. Furthermore, species variation in the pharmacology of the $\alpha_{2A}$-adrenoceptor exists. To date, subtype-selective alpha-2 adrenergic receptor ligands show only minimal selectivity or are nonselective with respect to other specific receptors, such that the therapeutic properties of subtype selective drugs are still under development.

A therapeutic field in which alpha-2 receptor agonists may be considered to have potential use is as an adjunct to anesthesia, for the control of pain and blockade of neurogenic inflammation. Sympathetic nervous system stimulation releases norepinephrine after tissue injury, and thus influences nociceptor activity. Alpha-2 receptor agonists, such as clonidine, can inhibit norepinephrine release at terminal nerve fibre endings and thus may induce analgesia directly at peripheral sites (without actions on the CNS). The ability of primary afferent neurons to release neurotransmitters from both their central and peripheral endings enables them to exert a dual, sensory and "efferent" or "local effector" function. The term, neurogenic inflammation, is used to describe the efferent function of the sensory nerves that includes the release of sensory neuropeptides that contribute, in a "feed-forward" manner, to the inflammatory process. Agents that induce the release of sensory neuropeptides from peripheral endings of sensory nerves, such as capsaicin, produce pain, inflammation and increased vascular permeability resulting in plasma extravasation. Drugs that block release of neuropeptides (substance P, CGRP) from sensory endings are predicted to possess analgesic and anti-inflammatory activity. This mechanism of action has been established for other drugs that exhibit analgesic and anti-inflammatory action in the periphery, such as sumatriptan and morphine, which act on 5HT1 and µ-opioid receptors, respectively. Both of these drugs are agonists that activate receptors that share a common mechanism of signal transduction with the alpha-2 receptors. UK14304, like sumatriptan, has been shown to block plasma extravasation within the dura mater through a prejunctional action on alpha-2 receptors.

Evidence supporting a peripheral analgesic effect of clonidine was obtained in a study of the effect of intra-articular injection of the drug at the end of an arthroscopic knee surgery ((Gentili, M et al (1996) Pain 64: 593-596)). Clonidine is considered to exhibit nonopiate anti-nociceptive properties, which might allow its use as an alternative for postoperative analgesia. In a study undertaken to evaluate the analgesic effects of clonidine administered intravenously to patients during the postoperative period, clonidine was found to delay the onset of pain and decrease the pain score. Thus, a number of studies have demonstrated intra- and postoperative analgesia effects from drugs acting either at alpha-2 adrenergic receptors, indicating these receptors are good therapeutic targets for new drugs to treat pain.

From the molecular and cellular mechanism of action defined for alpha-2 receptor agonists, such as UK14304, these compounds are expected to exhibit anti-nociceptive action on the peripheral terminals of primary afferent nerves when applied intraoperatively in an irrigation solution directly to tissues.

Alpha-2 receptor agonists are suitable for use in the current invention, delivered either as a single agent or in combination with other anti-pain and/or anti-inflammatory drugs, to inhibit pain and inflammation. Representative alpha-2 receptor agonists for the practice of the present invention include, for example: clonidine; dexmedetomidine; oxymetazoline; ((R)-(–)-3'-(2-amino-1-hydroxyethyl)-4'-fluoro-methane-sulfoanilide (NS-49); 2-[(5-methylbenz-1-ox-4-azin-6-yl) imino]imidazoline (AGN-193080); AGN 191103 and AGN 192172, as described in Munk, S. et al., J. Med. Chem. 39: 3533-3538 (1996); 5-bromo-N-(4,5-dihydro-1H-imidazol-2-yl)-6-quinoxalinamine (UK14304); 5,6,7,8-tetrahydro-6-(2-propenyl)-4H-thiazolo[4,5-d]azepin-2-amine (BHT920); 6-ethyl-5,6,7,8-tetrahydro-4H-oxaazolo[4,5-d]azepin-2-amine (BHT933), 5,6-dihydroxy-1,2,3,4-tetrahydro-1-naphyl-imidazoline (A-54741).

TABLE 19

Therapeutic and Preferred Concentrations of Alpha-2 Adrenergic Receptor Agonists

| Compounds | Therapeutic Acceptable Concentrations (nM) | Therapeutic Efficient Concentrations (nM) | Preferred Concentrations (nM) | Most Preferred Concentration (nM) |
| --- | --- | --- | --- | --- |
| clonidine | 0.002-200,000 | 0.01-50,000 | 0.1-10,000 | 10-2,000 |
| dexmedetomidine | 0.002-200,000 | 0.01-50,000 | 0.1-10,000 | 10-2,000 |
| UK14304 | 0.002-200,000 | 0.01-50,000 | 0.1-10,000 | 10-2,000 |
| oxymetazoline | 0.001-100,000 | 0.01-25,000 | 0.05-15,000 | 5-10,000 |
| NS-49 | 0.002-200,000 | 0.01-50,000 | 0.1-10,000 | 10-2,000 |
| AGN192172 | 0.005-100,000 | 0.1-25,000 | 1-5,000 | 10-1,000 |
| AGN193080 | 0.005-100,000 | 0.1-25,000 | 1-5,000 | 10-1,000 |
| AGN191103 | 0.002-200,000 | 0.1-25,000 | 1-5,000 | 10-1,000 |
| A-54741 | 0.002-200,000 | 0.1-50,000 | 1-10,000 | 10-2,000 |
| BHT920 | 0.003-200,000 | 0.3-50,000 | 3-30,000 | 30-5,000 |
| BHT933 | 0.003-200,000 | 0.3-50,000 | 3-30,000 | 30-5,000 |

F. Multi-Function Agents

In a further aspect of the present invention, selection of preferred agents to include in an ophthalmologic irrigation solution takes into consideration particular agents that display efficacy in more than one of the above functional classes. The previously described alpha-2 adrenergic receptor agonists provide examples of this, as they may function as both IOP reducing agents and agents that inhibit inflammation and pain. For example, oxymetazoline inhibits ocular inflammation by inhibiting release of sensory neurotransmitters (Fuder H., *J. Ocul. Pharmacol.*, 10:109-123 (1994)). Oxymetazoline also functions as a mydriatic agent via agonist activity at alpha-1-adrenergic receptors and also decreases IOP via agonist activity at alpha-2-adrenergic receptors (Chu T. et al, *Pharmacology*, 53:259-270 (1996)). NSAIDS, in addition to anti-inflammatory effects, also are indicated for inhibiting intra-operative miosis, thereby possessing mydriatic properties. Such multi-functional agents may suitably be used in the ophthalmologic solutions of the present invention when combined with an additional agent or agents that provide at least one additional ophthalmologic function not already provided by the multifunctional agent.

In addition to choosing multi-functional agents, avoiding toxic side-effects of these topically applied agents is also of importance. An advantage of topical delivery is a significant reduction in systemic side effects. However, local effects of these agents, such as reduced wound healing with high-concentration local anesthetics or steroids, must by considered. Therefore, local anesthetics at low concentrations that effectively inhibit neuronal discharge yet avoid wound-healing problems are preferred for use in the present invention (Bisla K, et al, *Invest. Ophthalmol. Vis. Sci.*, 33:3029-3033 (1992).). Because NSAIDS have been demonstrated to be as effective as steroids for controlling inflammation following ocular surgery (Dadeya S. et al, *J. Pediatr. Ophthalmol. Strabismus.*, 39:166-168 (2002)), NSAIDS are preferred to avoid the potential non-specific detrimental effects of steroids.

Depending on the specific requirements of various ophthalmologic surgical procedures, a variety of suitable irrigation solutions of the present invention including 2 or more agents may be formulated in accordance with the present invention, but each solution might not include agents drawn from all of the named functional categories (i.e., analgesic, anti-inflammatory, mydriati, and IOP reducing agents). For example, an irrigation solution formulated in accordance with the disclosure herein for use during cataract surgery may not require an analgesic, because this procedure is not as painful as a vitrectomy.

G. Irrigation Carriers

The active agents of the present invention are solubilized within a physiologic liquid irrigation carrier. The carrier is suitably an aqueous solution that may include physiologic electrolytes, such as normal saline or lactated Ringer's solution. More preferably, the carrier includes one or more adjuvants, and preferably all of the following adjuvants: sufficient electrolytes to provide a physiological balanced salt solution; a cellular energy source; a buffering agent; and a free-radical scavenger. One suitable solution (referred to in the examples below as a "preferred balanced salt solution" includes: electrolytes of from 50 to 500 millimolar sodium ions, from 0.1 to 50 millimolar potassium ions, from 0.1 to 5 millimolar calcium ions, from 0.1 to 5 millimolar magnesium ions, from 50 to 500 millimolar chloride ions, and from 0.1 to 10 millimolar phosphate; bicarbonate as a buffer at a concentration of from 10 to 50 millimolar; a cellular energy source selected from dextrose and glucose, at a concentration of from 1 to 25 millimolar; and glutathione as a free-radical scavenger (i.e., anti-oxidant) at a concentration of from 0.05 to 5 millimolar. The pH of the irrigation solution is suitable when controlled at between 5.5 and 8.0, preferably at a pH of 7.4.

VI. METHOD OF APPLICATION

The solution of the present invention has applications for a variety of operative/interventional procedures, including surgical, diagnostic and therapeutic techniques. The irrigation solution is applied perioperatively during ophthalmologic surgery. As defined above, the term "perioperative" encompasses application intraprocedurally, pre- and intraprocedurally, intra- and postprocedurally, and pre-, intra- and postprocedurally. Preferably, the solution is applied preprocedurally and/or postprocedurally as well as intraprocedurally. The irrigation solution is most preferably applied to the wound or surgical site prior to the initiation of the procedure, preferably before substantial tissue trauma, and continuously throughout a major portion or for the duration of the procedure, to preemptively block pain and inflammation, inhibit intraocular pressure increases, and/or cause mydriasis. As defined previously, continuous application of the irrigation fluid of the present invention may be carried out as an uninterrupted application, or repeated and frequent irrigation of wounds or procedural sites at a frequency sufficient to maintain a predetermined therapeutic local concentration of the applied agents, or an application in which there may be intermittent cessation of irrigation fluid flow necessitated by operating technique. At the conclusion of the procedure, additional amounts of the therapeutic agents may be introduced, such as by intraocular injection of an additional amount of the irrigation fluid including the same or a higher concentration of the active agents, or by intraocular injection or topical application of the agents in a viscoelastic gel.

The concentrations listed for each of the agents within the solutions of the present invention are the concentrations of the agents delivered locally, in the absence of metabolic transformation, to the operative site in order to achieve a predetermined level of effect at the operative site. This solution utilizes extremely low doses of these pain and inflammation inhibitors, due to the local application of the agents directly to the operative site during the procedure.

In each of the surgical solutions of the present invention, the agents are included in low concentrations and are delivered locally in low doses relative to concentrations and doses required with systemic methods of drug administration to achieve the desired therapeutic effect at the procedural site.

VII. EXAMPLES

The following are exemplary formulations in accordance with the present invention suitable for ophthalmologic procedures.

Example 1

Exemplary ophthalmologic solutions of the present invention for use during cataract removal surgery are described in Tables 20, 21 and 22. This solution, and the following solutions of Tables 23-25, are provided by way of example only, and are not intended to limit the invention. Anti-inflammatories are believed to be particularly useful in cataract solutions of the invention, to potentially reduce the post-operative incidence of, or hasten resolution of, cystoid macular edema (CME). These exemplary solutions and the other exemplary ophthalmologic irrigation solutions described herein below are provided in terms of the concentration of each agent included in the previously described preferred balanced-salt solution. The solution may suitably be supplied in 500 ml bags, this being the quantity of irrigation solution typically applied during a procedure, by way of non-limiting example.

TABLE 20

Exemplary Cataract Solution

| Class of Agent | Drug | Concentration (Nanomolar): Therapeutic | Preferred | Most Preferred |
|---|---|---|---|---|
| anti-inflammatory | flurbiprofen | 10-1,000,000 | 100-100,000 | 1,000-10,000 |
| IOP red. agent | timolol | 10-1,000,000 | 100-100,000 | 1,000-10,000 |
| mydriatic | phenylephrine | 50-500,000 | 500-100,000 | 1,000-10,000 |

TABLE 21

Alternate Exemplary Cataract Solution

| Class of Agent | Drug | Concentration (Nanomolar): Therapeutic | Preferred | Most Preferred |
|---|---|---|---|---|
| anti-inflammatory | ketoprofen | 10-1,000,000 | 100-100,000 | 1,000-10,000 |
| IOP red. agent | timolol | 10-1,000,000 | 100-100,000 | 1,000-10,000 |
| mydriatic | tropicamide | 10-1,000,000 | 100-100,000 | 1,000-10,000 |

TABLE 22

Alternate Exemplary Cataract Solution

| Class of Agent | Drug | Concentration (Nanomolar): Therapeutic | Preferred | Most Preferred |
|---|---|---|---|---|
| mydriatic, IOP red. agent | oxymetazoline | 10-1,000,000 | 100-100,000 | 1,000-10,000 |
| anti-inflammatory | flurbiprofen | 10-1,000,000 | 100-100,000 | 1,000-10,000 |

Example 2

A similar irrigation solution including multiple agents for effective reduction of inflammation and to provide mydriasis for invasive ophthalmologic surgery, such as a trabeculectomy, is provided in Table 23.

TABLE 23

Exemplary Trabeculectomy Solution

| Class of Agent | Drug | Concentration (Nanomolar): Therapeutic | Preferred | Most Preferred |
|---|---|---|---|---|
| anti-inflammatory | prednisolone | 10-1,000,000 | 100-100,000 | 1,000-10,000 |
| anti-inflammatory | flurbiprofen | 10-1,000,000 | 100-100,000 | 1,000-10,000 |
| IOP red. agent | timolol | 10-1,000,000 | 100-100,000 | 1,000-10,000 |
| mydriatic | phenylephrine | 50-500,000 | 500-100,000 | 1,000-10,000 |

Example 3

Irrigation solutions suitably used for extensive ophthalmologic surgery or posterior ocular chamber procedures, such as vitrectomy, provide increased analgesia by the addition of a local anesthetic. Such solutions of the present invention including a local anesthetic are provided in Tables 24 and 25.

TABLE 24

Exemplary Local Anesthetic Ophthalmologic Solution

| | | Concentration (Nanomolar): | | |
|---|---|---|---|---|
| Class of Agent | Drug | Therapeutic | Preferred | Most Preferred |
| IOP red. agent | timolol | 10-1,000,000 | 100-100,000 | 1,000-10,000 |
| anti-inflammatory | flurbiprofen | 10-1,000,000 | 100-100,000 | 1,000-10,000 |
| mydriatic | tropicamide | 10-1,000,000 | 100-100,000 | 1,000-10,000 |
| analgesic | lidocaine | 1,000-100,000,000 | 10,000-10,000,000 | 100,000-1,000,000 |

TABLE 25

Alternate Exemplary Local Anesthetic Ophthalmologic Solution

| | | Concentration (Nanomolar): | | |
|---|---|---|---|---|
| Class of Agent | Drug | Therapeutic | Preferred | Most Preferred |
| IOP red. agent | timolol | 10-1,000,000 | 100-100,000 | 1,000-10,000 |
| anti-inflammatory | flurbiprofen | 10-1,000,000 | 100-100,000 | 1,000-10,000 |
| mydriatic | tropicamide | 10-1,000,000 | 100-100,000 | 1,000-10,000 |
| analgesic | bupivacaine | 125-400,000 | 1,000-300,000 | 225,000-275,000 |

While the preferred embodiment of the invention has been illustrated and described, it will be appreciated that various changes to the disclosed solutions and methods can be made therein without departing from the spirit and scope of the invention. For example, alternate pain inhibitors, inflammation inhibitors, IOP reducing agents and mydriatic agents may be discovered that may augment or replace the disclosed agents in accordance with the disclosure contained herein. It is therefore intended that the scope of Letters Patent granted hereon be limited only by the definitions of the appended claims.

The embodiments of the invention in which an exclusive property or privilege is claimed are defined as follows:

1. A method of irrigation during an intraocular ophthalmologic procedure, comprising irrigating intraocular tissues during an intraocular ophthalmologic procedure with a solution including at least an anti-inflammatory agent and a mydriatic agent in a liquid irrigation carrier, wherein the anti-inflammatory agent comprises ketorolac and the mydriatic agent comprises phenylephrine and the agents are included in a therapeutically effective amount for the maintenance of mydriasis during the procedure and the reduction of postoperative pain when delivered intraocularly during the intraocular ophthalmologic procedure.

2. The method of claim 1, wherein the ketorolac is included in the solution at a concentration of no more than 100,000 nanomolar and the phenylephrine is included in the solution at a concentration of no more than 500,000 nanomolar.

3. The method of claim 1, wherein each of the agents contributes to the maintenance of intraoperative mydriasis by providing for mydriasis or inhibiting miosis.

4. The method of claim 1, wherein the solution further comprises an analgesic agent selected from the group consisting of local anesthetics and opioids.

5. The method of claim 4, wherein: the local anesthetic, if selected, is selected from the group consisting of lidocaine, tetracaine, bupivacaine, and proparacaine; and the opioid, if selected, is selected from the group consisting of morphine, fentanyl and hydromorphone.

6. The method of claim 1, wherein the solution further comprises an agent for decreasing intraocular pressure ("IOP reducing agent") selected from the group consisting of beta adrenergic receptor antagonists, carbonic anhydrase inhibitors, alpha-2 adrenergic receptor agonists, and prostaglandin agonists.

7. The method of claim 6, wherein: the beta adrenergic receptor antagonist, if selected, is selected from the group consisting of timolol, metipranolol and levobunolol; the carbonic anhydrase inhibitor, if selected, is selected from the group consisting of brinzolamide and dorzolamide; the alpha-2 adrenergic receptor agonist, if selected, is selected from the group consisting of apraclonidine, brimonidine and oxymetazoline; and the prostaglandin agonist, if selected, is selected from the group consisting of latanoprost, travoprost and bimatoprost.

8. The method of claim 1, wherein the solution is continuously applied to the intraocular tissues during the intraocular procedure.

9. The method of claim 1, wherein the liquid irrigation carrier further comprises an adjuvant selected from electrolytes sufficient to provide a physiological balanced salt solution, a cellular energy source, a buffering agent, a free-radical scavenger and mixtures thereof.

10. The method of claim 9, wherein: the electrolytes, if selected, comprise from 50 to 500 millimolar sodium ions, from 0.1 to 50 millimolar potassium ions, from 0.1 to 5 millimolar calcium ions, from 0.1 to 5 millimolar magnesium ions, from 50 to 500 millimolar chloride ions, and from 0.1 to 10 millimolar phosphate; the buffer, if selected, comprises bicarbonate at a concentration of from 10 to 50 millimolar; the cellular energy source if selected, is selected from dextrose and glucose and is present at a concentration of from 1 to 25 millimolar; and the free-radical scavenger, if selected, comprises glutathione at a concentration of from 0.05 to 5 millimolar.

11. The method of claim 1, wherein the liquid irrigation carrier further comprises electrolytes sufficient to provide a physiological balanced salt solution, a cellular energy source, a buffering agent and a free-radical scavenger.

12. The method of claim 11, wherein: the electrolytes comprise from 50 to 500 millimolar sodium ions, from 0.1 to 50 millimolar potassium ions, from 0.1 to 5 millimolar calcium ions, from 0.1 to 5 millimolar magnesium ions, from 50 to 500 millimolar chloride ions, and from 0.1 to 10 millimolar phosphate; the buffer comprises bicarbonate at a concentration of from 10 to 50 millimolar; the cellular energy source is selected from dextrose and glucose and is present at a concentration of from 1 to 25 millimolar; and the free-radical scavenger comprises glutathione at a concentration of from 0.05 to 5 millimolar.

13. The method of claim 1, wherein the pH of the irrigation solution is between 5.5 and 8.0.

\* \* \* \* \*